US011237084B2

(12) United States Patent
Fortin et al.

(10) Patent No.: US 11,237,084 B2
(45) Date of Patent: Feb. 1, 2022

(54) SOLUBLE BALLS FOR PREPARING SOLUTIONS

(71) Applicant: ANAQUANT, Villeurbanne (FR)

(72) Inventors: Tanguy Fortin, Lyons (FR); Chloe Bardet, Lyons (FR); Jordane Biarc, Lyons (FR)

(73) Assignee: ANAQUANT, Villeurbane (FR)

( * ) Notice: Subject to any disclaimer, the term of this patent is extended or adjusted under 35 U.S.C. 154(b) by 92 days.

(21) Appl. No.: 16/087,530

(22) PCT Filed: Mar. 23, 2017

(86) PCT No.: PCT/EP2017/056949
§ 371 (c)(1),
(2) Date: Sep. 21, 2018

(87) PCT Pub. No.: WO2017/162801
PCT Pub. Date: Sep. 28, 2017

(65) Prior Publication Data
US 2019/0101476 A1   Apr. 4, 2019

(30) Foreign Application Priority Data

Mar. 23, 2016  (FR) ...................................... 1652478

(51) Int. Cl.
*G01N 1/28*      (2006.01)
*C07K 17/10*    (2006.01)
(Continued)

(52) U.S. Cl.
CPC ............... *G01N 1/28* (2013.01); *C07K 17/10* (2013.01); *G01N 30/62* (2013.01); *G01N 30/72* (2013.01);
(Continued)

(58) Field of Classification Search
CPC .... C12Q 1/32; G01N 1/28; G01N 2001/2893; G01N 21/91; G01N 2333/765;
(Continued)

(56) References Cited

U.S. PATENT DOCUMENTS 4,070,348 A * 1/1978 Kraemer ................... C08F 2/14
526/273
4,703,717 A   11/1987 Abecassis et al.
(Continued)

FOREIGN PATENT DOCUMENTS

FR     2574659 A1   6/1986
WO   WO9807411 A1   2/1998
(Continued)

OTHER PUBLICATIONS

International Search Report of PCT/EP2017/056949; dated Jun. 6, 2017; Feike Liefrink.

*Primary Examiner* — Jennifer Wecker
(74) *Attorney, Agent, or Firm* — BCF, LLP

(57) ABSTRACT

The present invention concerns the preparation of solutions, particularly for implementing analytical methods, in particular by spectrometry, particularly for producing standard solutions which are useful, for example, for calibrating spectrometers or for implementing diagnostic methods. It allows the implementation of an easy process for preparing such standard solutions.

21 Claims, 2 Drawing Sheets
Specification includes a Sequence Listing.

(51) Int. Cl.
*G01N 30/62* (2006.01)
*G01N 30/72* (2006.01)

(52) U.S. Cl.
CPC ............... *G01N 2001/2893* (2013.01); *G01N 2030/626* (2013.01)

(58) Field of Classification Search
CPC ........... G01N 2496/00; G01N 2496/80; G01N 33/96; G01N 2030/626; G01N 30/62; G01N 30/72; A23B 4/033; A23B 4/08; A23B 4/10; A23B 4/20; A23B 7/022; A23B 7/154; A23B 7/16; A23J 3/18; A23L 29/231; A23L 29/238; A23L 29/25; A23L 29/256; A23L 29/27; A23L 33/21; A23L 3/42; A23P 10/30; E01C 7/142; E01C 7/26; E01C 7/36; E02B 3/126; C07K 17/10
See application file for complete search history.

(56) References Cited

U.S. PATENT DOCUMENTS

| | | | | |
|---|---|---|---|---|
| 5,591,473 A | * | 1/1997 | McArdle | A23B 4/033 426/103 |
| 2008/0090295 A1 | | 4/2008 | Feuerstein | |
| 2009/0029870 A1 | * | 1/2009 | Ward | G01N 21/64 506/9 |
| 2013/0040857 A1 | * | 2/2013 | Anderson | C07K 7/06 506/12 |
| 2013/0221281 A1 | * | 8/2013 | Ebrahim | G01N 33/96 252/408.1 |

FOREIGN PATENT DOCUMENTS

| | | |
|---|---|---|
| WO | WO03008547 A2 | 1/2003 |
| WO | WO2010035504 A1 | 4/2010 |
| WO | WO2013043388 A1 | 3/2013 |
| WO | WO2014066284 A1 | 5/2014 |

* cited by examiner

SOLUBLE BALLS FOR PREPARING SOLUTIONS

CROSS-REFERENCE TO RELATED APPLICATIONS

This Application is a United States National Stage Patent Application of International Application No. PCT/EP2016/056949, filed on Mar. 23, 2017 which claims priority from French Patent Application No. 1652478, filed Mar. 23, 2016, the content of both of which is herein incorporated in their entirety by reference.

FIELD OF INVENTION

The present invention concerns the preparation of solutions, particularly for implementing analytical methods, in particular by spectrometry, particularly for producing standard solutions which are useful, for example, for calibrating spectrometers or for implementing diagnostic methods. It allows the implementation of an easy process for preparing such standard solutions.

STATE OF THE ART

Figure 1:
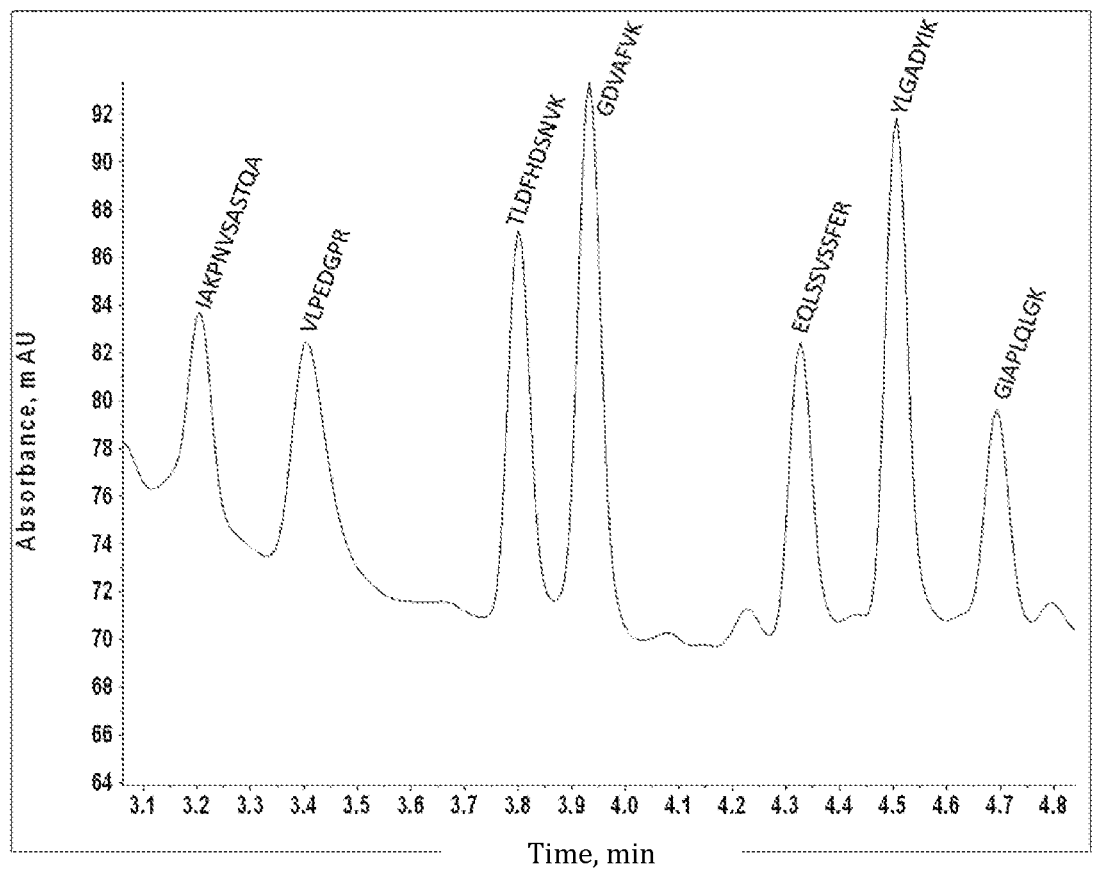
FIG. 1 is a graph representing the chromatogram of a solution prepared from dissolving a saccharose bead grafted on its surface with seven different peptides.

Spectrometers must be calibrated before use to ensure that they function properly and that the results are accurate, and in order to perform quantitative spectrometry methods.

For example, known methods include the quantitative analysis of proteins by mass spectrometry using labelled product lines requiring the preparation of standard solutions (EP 1 456 227, WO 2010/035504, WO 2014/066284). The preparation of such standard solutions is often time-consuming and requires special attention to ensure good reproducibility of results over time and good stability.

Likewise, the preparation of reagent solutions for chemical or enzymatic reactions in predetermined amounts could be simplified if simple means were available for preparing standard solutions which preserve the activity of these reagents, chemical molecules or enzymes.

Application WO 2013/043388 describes the preparation by lyophilization of particles consisting essentially of proteins to be dissolved with salt, a buffer and a bulking agent. This lyophilization technique does not make it possible to produce calibrated particles which can be used for the preparation of standard solutions.

U.S. Pat. No. 5,591,473 describes the preparation of a protein-polysaccharide complex, well known to the skilled person, but does not describe the preparation of such complexes for the preparation of calibrated beads.

The present invention makes it possible to solve this technical problem with soluble beads carrying at least one product to be solubilized grafted onto their surface.

DISCLOSURE OF THE INVENTION

The invention concerns a process for preparing a solution of at least one product to be dissolved, in particular to be dissolved in a predetermined amount, particularly for the analysis thereof by spectrometry, characterized in that it comprises dissolving, in the solvent of the solution, one or more soluble beads on whose surface said at least one product to be dissolved is grafted, in particular for the analysis thereof.

It also concerns a set of soluble beads carrying at least one product to be dissolved grafted onto their surface, characterized in that the beads each have a predetermined amount of product grafted onto their substantially equal surface, in particular a set whose beads are packaged in the same packaging allowing controlled release of the number of beads, and by this means allowing control of the amount of product to be dissolved.

The invention also concerns a range of products to be dissolved, characterized in that it comprises at least two sets of beads according to the invention, each set having a predetermined amount of grafted product different from the other sets.

DETAILED DESCRIPTION OF THE INVENTION

The present invention concerns a process for preparing a solution of at least one product, characterized in that it comprises dissolving, in the solvent of the solution, one or more soluble beads on whose surface said at least one product is grafted.

According to the invention, "bead", or also "grain", means any potato-shaped solid particulate carrier that can pass through a sieve. However, the objective being to prepare standard solutions, the skilled person will preferably choose beads of homogeneous shape, particularly ovoids, preferably essentially round.

The beads are advantageously calibrated with a homogeneous diameter, preferably from 1 to 4 mm. Measurement of the diameter of beads is well known to the skilled person. It preferably being a matter of industrially produced beads, the average diameter of a set of beads produced in the same batch is generally homogeneous, with a margin of error of less than 5%, preferably less than 3%. The diameter of the beads can be controlled by the use of sieves allowing a margin of error of 5%, or even 3%, of the expected size.

The skilled person is well familiar with the components of beads and will be able to choose them based on the solvent used in the solutions and the use of the solution obtained, in particular for spectrometry, and for a product to be analysed, the nature of the product and the spectrometry method. Indeed, the components of the beads must not interfere with the grafted products after dissolution, and especially with the spectrometers and the results obtained.

According to the invention, "grafted" means any interaction between the carrier and the product which makes it possible to bind the product to its carrier during storage (dry product) and facilitates the release of the product after dissolution of the carrier. This bond can be a strong or weak physicochemical bond, in particular an adsorption of the product onto the surface of the carrier. It is important that the product/carrier bond is broken in such a way that the product is substantially completely released into the solution. The skilled person will be able to determine this complete release by comparing the expected concentration of product in the solution with the measured concentration.

The solvent of the solutions is usually water or a hydroalcoholic solution, preferably water.

The bead is advantageously constituted of one or more water-soluble compounds chosen among sugars, polysaccharides, hydroxycarboxylic acids, and mixtures thereof, in particular chosen among sucrose, lactose, alginates, lactic acid and mixtures thereof.

Particular mention may be made of the beads used as carriers for homeopathic preparations, well known to the skilled person, notably described in WO 98/07411.

Advantageously, the amount of product grafted onto each bead is predetermined so that each bead of a set of beads comprises substantially the same amount of product, thus allowing the skilled person to know the amount of product in the solution by simply multiplying by the number of beads dissolved in the solution.

The amount of product ranges from 1 picogram to 100 micrograms per bead.

The process according to the invention is particularly suitable for preparing solutions of products to be analysed, more particularly by spectroscopy.

Of course, the process according to the invention is suitable for the easy preparation of solutions of products of predetermined concentrations, regardless of the purpose of said solutions.

"Product to be dissolved" means any product whose dissolution makes it possible to produce solutions of predetermined concentrations, such as chemical molecules, peptides or proteins, particularly enzymes.

According to a particular embodiment, the invention concerns a process for preparing a solution of at least one product to be analysed by spectrometry, characterized in that it comprises dissolving, in the solvent of the solution, one or more soluble beads on whose surface said at least one product to be analysed is grafted.

According to another particular embodiment, the invention concerns a process for preparing a solution of at least one active enzyme, characterized in that it comprises dissolving, in the solvent of the solution, one or more soluble beads on whose surface the at least one enzyme whose activity has been preserved is grafted.

The skilled person knows the various products which can be used to prepare solutions of predetermined concentrations, in particular for spectrometric analyses, particularly as calibration products, or to prepare enzyme solutions. Particular mention may be made of peptides, proteins and small molecules. The grafted molecules may be isotopically labelled, deuterated or contain modifications such as phosphorylation, oxidation, carbamidomethylation or any other known post-translational modifications in peptides or proteins. The grafted molecules can be chemically synthesized and then, purified or not, adsorbed onto the polymeric carrier. The molecules can also be purified directly from biological samples before being grafted onto the polymeric carriers or be added grafted during production via successive layers of the polymeric carriers.

The bead according to the invention may comprise several grafted products, each in predetermined proportions, independent of each other. The same bead may have 2, 3, 5, 10, 20 or 30 or more different products grafted onto its surface. A bead grafted with more than 70 different products was prepared according to the present invention.

Among the products that can be grafted, alone or in combination, mention may be made of peptides or small organic molecules, particularly products having therapeutic activity, such as antibiotics, in particular the following products:

| Peptide sequence/ Molecule name | Peptide sequence/ Molecule name | Peptide sequence/ Molecule name | Peptide sequence/ Molecule name | Peptide sequence/ Molecule name |
|---|---|---|---|---|
| EGVLYVGSK | Bitertanol | TFDPYYAVALVK | Isoprocarb | VQIINK |
| EGVVAAAEK | Boscalid | FTDPVNIISVYK | Isoproturon | VQIVY [Pho] KPVDLSK |
| EGVVHGVTTVAEK | Bromucanozole | LGDPLGADVAQVTGALR | Ivermectin | AVFVDLEPTVIDEVR |
| EQVTNVGGAVVTGVTAVAQK | Bupirimate | GIDPEAVLADLR | Kresoxim-methyl | VGINYQPPTVVPGGDLAK |
| QGVAEAAGK | Buprofezin | YDPLVVFSHGLGAFR | Linuron | VAPEEHPVLLTEAPLNPK |
| TVEGAGNIAAATGFVK | Butafenacil | QDPNEILIFWSK | Lufenuron | GYSFTTTAER |
| AEEAGIGDTPNQEDQAAGHVT[Pho] QAR | Butocarboxim | EQDPVTNVGGAVVTGVTAVAQK | Mandipropamid | DVNAAIAAIK |
| AEEAGIGDTPNQEDQAAGHVTQAR | Butoxy-carboxim | IDPGSSDGSSSR | Mefenacet | EIIDPVLDR |
| AEEAGIGDTPSLEDEAAGHVT[Pho] QAR | Carbaryl | EGDPVVAAAEK | Mepanipyrim | DSYVGDEAQSK |

-continued

| Peptide sequence/ Molecule name | Peptide sequence/ Molecule name | Peptide sequence/ Molecule name | Peptide sequence/ Molecule name | Peptide sequence/ Molecule name |
|---|---|---|---|---|
| AEEAGIGDTPS LEDEAAGHVTQ AR | Carbendazim | EADPNYIGSDK | Mepronil | AVFPSIVGRPR |
| C[CAM] GSLGN IHHKPGGGQVE VK | Carbetamide | SQDPTVLQNTGGR | Mesotrione | GIAPLQLGK |
| DRTGNDEK | Carbofuran | SGDPGVCLNCR | Metaflumizone | LHTFGDENEDDSE LAR |
| ES[Pho] PLQT PTEDGSEEPGS ETSDAK | Carboxin | ATDPFNPAQDK | Metalaxyl | SGGVCLNCR |
| ES[Pho] PPQP PADDGAEEPGS ETSDAK | Carfentrazone-ethyl | ANDPIGATLNR | Metconazole | SPIAPCIK |
| ESPLQTPTEDG SEEPGSETSDA K | Chlorantran-iliprole | LYYDPSQDNDR | Methabenz-thiazuron | SSLVIQWR |
| ESPPQPPADDG AEEPGSETSDA K | Chlorfluazuron | SDPIAPCIK | Methamido-phos | gentamicin |
| GAAPPGQK | Chlorotoluron | SLADPAVVTGK | Methiocarb | FDPVHAALVWGPE K |
| GAASPAQK | Chloroxuron | TLDPFSR | Methomyl | SYDPYWIGIR |
| HLSNVSSTGSI DMVDSPQLATL ADEVSASLAK | Clethodim | LHDPTFGDENEDD SELAR | Methoprotryne | Flusilazole |
| HVLGGGSVQIV YKPVDLSK | Clofentezine | ASDPYLDCIK | Methoxy-fenozide | Flutolanil |
| HVPGGGSVQIV YKPVDLSK | Clothianidin | IGDPSLDNITHVP GGGNK | Metobromuron | Flutriafol |
| IATPRGAAPPG QK | Cyazofamid | ADPAATVVDVDEV R | Metribuzin | Forchlorfenuron |
| IATPRGAASPA QK | Cycluron | VDPSVYPLDR | Mevinphos | Formetanate HCL |
| IGS[Pho] LDN ITHVPGGGNK | Cymoxanil | EGDPYYGYTGAFR | Mexacarbate | Fuberidazole |
| IGS[Pho] TENLK | Cyproconazole | DSDPAYGFFK | Monocrotophos | Furalaxyl |
| IGSLDNITHVP GGGNK | Cyprodinil | VEDPSWILR | Monolinuron | Furathiocarb |
| IGSTENLK | Cyromazine | SSDPLVIQWR | Moxidectin | Halofenozide |
| LDLSNVQS [Pho] K | Desmedipham | CIPDFVNAAFGK | Myclobutanil | Hexaconazole |
| LDLSNVQSK | Diclobutrazol | Tacrolimus | Neburon | Hexaflumuron |
| LQTAPVPMPDL K | Dicrotophos | Sirolimus | Nitenpyram | Hexythiazox |
| QEFDTMEDHAG DYTLLQDQEGD MDHGLK | Diethofencarb | Everolimus | Novaluron | Hydramethylnon |

-continued

| Peptide sequence/ Molecule name | Peptide sequence/ Molecule name | Peptide sequence/ Molecule name | Peptide sequence/ Molecule name | Peptide sequence/ Molecule name |
|---|---|---|---|---|
| QEFEVM[Oxi]EDHAGTYGLGDR | Difenoconazole | TCTTPAQGNSMFPSCCCTKPTDGNCTCIPIPSSWAFAK | Nuarimol | Imidacloprid |
| QEFEVMEDHAGTYGLGDR | Diflubenzuron | TCTTPAQGNSMFPSCCCTKPTD | Omethoate | Indoxacarb |
| S[Pho]PVVSGDTS[Pho]PR | Dimethoate | GNCTCIPIPSSWAFAK | Oxadixyl | Ipconazole |
| S[Pho]PVVSGDTSPR | Dimethomorph | KTCTTPAQGNSMFPSCCCT | Oxamyl | Iprovalicarb |
| S[Pho]TPT[Pho]AEDVTAPLVDEGAPGK | Dimoxystrobin | KPTDGNCTCIPIPSSWAFA | Paclobutrazol | Isocarbophos |
| S[Pho]TPT[Pho]AEDVTAPLVDER | Diniconazole | TCTTPAQGNSMFPSCCCTK | Penconazole | GIAPLQLGK |
| S[Pho]TPTAEDVTAPLVDEGAPGK | Dinotefuran | PTDGNCTCIPIPSSWAFAK | Pencycuron | IAKPNVSASTQASR |
| S[Pho]TPTAEDVTAPLVDER | Dioxacarb | LGPLV*EQGR | Phenmedipham | TLDFHDSNVK |
| SGYSSPGS[Pho]PGT[Pho]PGSR | Diuron | LGATQSNEITIPVTFESR | Picoxystrobin | VLPEDGPR |
| SGYSSPGS[Pho]PGTPGSR | Doramectin | NGVPQEESLEDSDVDADFK | Piperonyl butoxide | YLGADYIK |
| SGYSSPGSPGT[Pho]PGSR | Emamectin-benzoate | LGASVPGSQTVVVK | Pirimicarb | 3-Hydroxycar-bofuran |
| SGYSSPGSPGTPGSR | Epoxiconazole | NGISQVLEK | Prochloraz | Abamectin |
| SPVVSGDTS[Pho]PR | Eprinomectin | NGFSIQVR | Promecarb | Acephate |
| SPVVSGDTSPR | Etaconazole | DGVTLQK | Prometon | Acetamiprid |
| STPT[Pho]AEDVTAPLVDEGAPGK | Ethiofencarb | SGIPDNAFQSFGR | Propamocarb | Acibenzolar-S-methyl |
| STPT[Pho]AEDVTAPLVDER | Ethiprole | LGLIFDTSNLQSGVPSR | Propargite | Alanycarb |
| STPTAEDVTAPLVDEGAPGK | Ethirimol | LGPQTLSR | Propham | Aldicarb |
| STPTAEDVTAPLVDER | Ethofumesate | EGQLTPLIK | Propiconazole | Aldicarb sulfone |

-continued

| Peptide sequence/ Molecule name | Peptide sequence/ Molecule name | Peptide sequence/ Molecule name | Peptide sequence/ Molecule name | Peptide sequence/ Molecule name |
|---|---|---|---|---|
| T [Pho] PPGS [Pho] GEPPK | Etoxazole | EGFDDLPLAEQR | Propoxur | Aldicarb sulfoxide |
| T [Pho] PPGSG EPPK | Famoxadone | TGQSSLVPALTDFVR | Prothioconazole | Ametryn |
| T [Pho] PPSS [Pho] GEPPK | Fenamidone | GGFPEFVNELHNNGQK | Pymetrozine | Aminocarb |
| T [Pho] PPSSG EPPK | Fenarimol | EGAQLPVIENK | Pyracarbolid | Amitraz |
| T [Pho] PS [Pho] LPTPPTR | Fenazaquin | AGIPNNQVLGK | Pyraclostrobin | Azoxystrobin |
| TDHGAEIVY [Pho] K | Fenbuconazole | ALVQIVGK | Pyridaben | Tebufenpyrad |
| TDHGAEIVYK | Fenhexamid | GHSGLQPGR | Pyrimethanil | Tebuthiuron |
| TPPGS [Pho] G EPPK | Fenobucarb | ASTPGAAAQIQEVGK | Pyriproxyfen | Teflubenzuron |
| TPPGSGEPPK | Fenoxycarb | VVNPTQGK | Quinoxyfen | Temephos |
| TPPSS [Pho] G EPPK | Fenpropimorph | IPLENLQIIGR | Rotenone | Terbumeton |
| TPPSSGEPPK | Fenpyroximate | NLAVQAQGK | Secbumeton | Terbutryn |
| TPS [Pho] LPT PPTR | Fenuron | VLDALQAIGK | Siduron | Tetraconazole |
| TPSLPTPPTR | Fipronil | VTEPISAESGEQVEGR | Simetryn | Thiabendazole |
| VAVVRT [Pho] PPK | Flonicamid | ISPNTSQQNFVTQGR | Spinetoram | Thiacloprid |
| VAVVRTPPK | Fluazinam | FQAFANGSLLIPDFGGK | Spinosad | Thiamethoxam |
| VQIVYKPVDLSK | Flubendimide | EPISVSSEQVLGK | Spirodiclofen | Thidiazuron |
| HLSNVSS [Pho] TGSIDMVDSPQLATLADEVSASLAK | Fludioxonil | AVFQANQENLPILGK | Spiromesifen | Thiobencarb |
| HVPGGGSVQIVY [Pho] KPVDLSK | Flufenacet | VQPVSEILQLGK | Spirotetramat | Thiofanox |
| HVSGGGSVQIVYKPVDLSK | Flufenoxuron | ALDVIQAGGK | Spiroxamine | Thiophanate-methyl |
| SGYSS [Pho] PGSPGTPGSR | Fluometuron | IIHESGAQILGR | Sulfentrazone | Triadimefon |

| Peptide sequence/ Molecule name | Peptide sequence/ Molecule name | Peptide sequence/ Molecule name | Peptide sequence/ Molecule name | Peptide sequence/ Molecule name |
|---|---|---|---|---|
| T[Pho] PSLPT PPTR | Fluoxastrobin | EQLSSVSSFER | Tebuconazole | Triadimenol |
| TPSLPT [Pho] PPTR | Fluquinco-nazole | GDVAFVK | Tebufenozide | Trichlorfon |

Among the products that can be grafted, alone or in combination, mention may be made of proteins, in particular enzymes such as trypsin, chymotrypsin, papain, pepsin or any other peptidases. Any protein for which the skilled person wishes to prepare solutions of a predetermined amount without denaturation falls within the scope of the present invention.

The preparation of such beads and the methods for impregnating same with reagents are well known to the skilled person, in particular by adapting the usual methods for preparing beads for homeopathic medicines (FR 2 574 659, WO 98/07411).

The beads are placed in a glass container whose size is proportional to the diameter of the beads. Advantageously, the volume of the container must be 5 times greater than the total volume represented by the beads, for example, 50 3-mm beads in a 4-cm diameter container.

The stock solution of the products, molecules, to be grafted is composed of more than 70% organic solvent such as methanol or acetonitrile. The beads are brought into contact with the stock solution with a proportion of 1 g of beads per 100 µL of stock solution which may contain acid to promote adsorption of the molecules onto the polymer beads.

The grafting process is preferably carried out under continuous stirring to guarantee homogeneous adsorption of the molecules on all the beads of a production batch. The manufacturing process can be broken down into two steps, a first step consisting in impregnating polymer beads with a solution containing the one or more molecules to be grafted, then a second step of drying the polymer beads.

Impregnation is preferably carried out under stirring in a glass container, in particular at a pressure of 300 mbar to 800 mbar, preferably about 600 mbar, and at a temperature of 20° C. to 60° C., preferably about 40° C., for a period of between 10 and 40 minutes, preferably about 20 minutes.

After impregnation, the beads are preferably dried under a controlled atmosphere at a pressure ranging from 300 mbar to 800 mbar, preferably about 600 mbar, at a temperature ranging from 20° C. to 60° C., preferably about 40° C., advantageously by a stream of gas, which may be compressed air, nitrogen or any other inert gas, for example entering through a tube whose end is at the opening of the glass bottle containing the beads, for a period advantageously of between 10 and 40 minutes, preferably about 10 minutes.

This impregnation and drying cycle can be repeated several times, advantageously at least three times, to guarantee homogeneous grafting of the molecules onto the polymer beads.

When there are several grafted products, they can be either grafted together, from a stock solution comprising them all, or grafted in several successive groups, each comprising one or more products.

The invention also concerns a set of soluble beads carrying a product to be analysed grafted onto their surface, as described above and in the examples, characterized in that the beads each have a predetermined amount of product adsorbed onto their substantially equal surface.

Advantageously, this set of beads is packaged in packaging that allows controlled release of the number of beads. Such packaging, well known to the skilled person, is notably used for releasing beads of homeopathic compositions, food products such as aspartame tablets, or sweets.

The invention also concerns a range of products to be analysed, characterized in that it comprises at least two sets of beads according to the invention, each set having a predetermined amount of grafted products different from the other sets.

The difference in the amounts of grafted products between the different sets will depend on the use of these sets. The predetermined amounts of each set can be chosen so as to be separated for example by a factor of 2, or a factor of 10, or according to a logarithmic rule.

Such a product range can be employed to prepare external calibration standards used for quantifying compounds or for measuring compounds in samples having different concentration levels of the compound to be analysed.

The grafted beads can have various uses, they can be used for absolute quantification of compounds.

The grafted beads can also be used to release a standard allowing relative quantification between samples, thus the beads will be used to normalize the results of the analysis of the samples.

They can also be used to release compounds used for quality control of measuring instruments such as spectrometers.

The grafted beads can be used to release compounds useful for detecting biological mechanisms such as immune reactions or competition between an antibody and an antigen, or for evaluating the toxicity of compounds on biological models, particularly for analyses in the field of diagnostics.

Advantageously, the beads can be employed in the first steps of sample preparation, in an intermediate step of sample preparation, or at the end of sample preparation before analysis of the final sample.

EXAMPLES

Example 1—Preparation of Beads Grafted with Peptides

A stock solution of peptide is prepared by taking up 200 µg of peptide GDVAFVK lysine (K)-labelled with heavy isotopes 13C and 15N in 1 mL of a methanol 0.5% formic acid solution. 100 μL of this stock solution is taken and added to 900 μL of methanol to obtain a 20 μg/mL solution. Fifty 3-mm diameter saccharose beads are placed in a 25-mL volume glass round-bottom flask. 100 μL of the 20 μg/mL solution is placed in the flask containing the sucrose beads.

The glass round-bottom flask containing the beads and the peptide solution is rotated and placed under vacuum to a pressure of 600 mbar for 20 minutes. At the end of this impregnation period, compressed air is injected into the flask at a flow rate of 12 L/min for 10 minutes under a constant vacuum of 600 mbar. After this first impregnation/drying cycle, it is repeated twice for a total of three complete cycles.

A bead grafted with peptide GDVAFVK is taken up in 500 μL of a 95% H₂O, 5% ACN, 0.5% formic acid solution then solubilized for 2 minutes.

A 40 μL volume of the sample obtained is injected and analysed according to the following conditions:

Agilent 1290 chromatography system (Les Ulys, France)
Phenomenex Aeris peptide C18 column, 2.1 mm internal diameter, 100 mm in length, 3.6 mm particle size
Solvent A: H₂O+0.1% formic acid
Solvent B: ACN+0.1% formic acid
Liquid chromatography gradient as follows:

| min | Flow (μL/min) | Solvent A | Solvent B |
|---|---|---|---|
| 0 | 300 | 95 | 5 |
| 1 | 300 | 95 | 5 |
| 8 | 300 | 50 | 50 |
| 8.1 | 300 | 5 | 95 |
| 12 | 300 | 5 | 95 |
| 12.1 | 300 | 95 | 5 |
| 15 | 300 | 95 | 5 |

The eluate leaving the chromatographic column is injected directly into an Agilent 1290 diode array detector. UV absorption is measured at a wavelength of 205 nm.

The eluate leaving the chromatographic column can also be injected directly into the ionization source of a Sciex QTRAP® 5500 mass spectrometer (Foster City, USA). The following machine parameters are used:

Scan type: MRM
Polarity: Positive
Ionization source: Turbo V (Sciex)
Precursor: 372.2
Ion fragment: 472.3
Ion fragment: 401.3
Ion fragment: 571.4
Setting Q1: Filtering with unit resolution
Setting Q3: Filtering with unit resolution
Cone voltage: 5500 V
Source temperature: 500.00° C.
Nebulizer gas: 50.00 psi
Heating gas: 40.00 psi
Curtain gas: 50.00 psi This protocol can also be applied to other types of molecules such as pesticides, antibiotics or any other small molecule.

Example 2—Preparation of Beads Grafted with 7 Peptides (FIG. 1)

The following 7 peptides were grafted onto sucrose beads:

| | |
|---|---|
| GIAPLQLG | [K(13C6; 15N2)] |
| EQLSSVSSFE | [R(13C6; 15N4)] |
| TLDFHDSNV | [K(13C6; 15N2)] |
| VLPEDGP | [R(13C6; 15N4)] |
| GDVAFV | [K(13C6; 15N2)] |
| YLGADYI | [K(13C6; 15N2)] |
| IAKPNVSASTQAS | [R((13C6); 15N4)] |

A 200 μg aliquot of the first peptide is dissolved in 1 mL of methanol. The solution is added to the 200 μg of the second peptide, then the latter is added to the 200 μg of the third peptide, and so on, until the seventh and last peptide, to obtain a mixture of 7 peptides each with a concentration of 200 μg/mL.

1.8 mL of methanol is added to the 200 μg/mL stock solution to obtain a 70 μg/mL solution. 100 μL of this solution is added to 250 μL of methanol to obtain a 20 μg/mL solution for each of the peptides.

The grafting protocol described in Example 1 is carried out to obtain beads grafted with the 7 peptides.

A bead grafted with the 7 peptides is taken up in 500 μL of a 95% H₂O, 5% ACN, 0.5% formic acid solution then solubilized for 2 minutes.

A 40 μL volume of the sample obtained is injected and analysed according to the following conditions:

Agilent 1290 chromatographic system (Les Ulys, France)
Phenomenex Aeris peptide C18 column, 2.1 mm internal diameter, 100 mm in length, 3.6 mm particle size
Solvent A: H₂O+0.1% formic acid
Solvent B: ACN+0.1% formic acid
Liquid chromatography gradient as follows:

| min | Flow (μL/min) | Solvent A | Solvent B |
|---|---|---|---|
| 0 | 300 | 95 | 5 |
| 1 | 300 | 95 | 5 |
| 8 | 300 | 50 | 50 |
| 8.1 | 300 | 5 | 95 |
| 12 | 300 | 5 | 95 |
| 12.1 | 300 | 95 | 5 |
| 15 | 300 | 95 | 5 |

The eluate leaving the chromatographic column is injected directly into an Agilent 1290 diode array detector. UV absorption is measured at a wavelength of 205 nm. The result is shown in FIG. 1.

Figure 2:
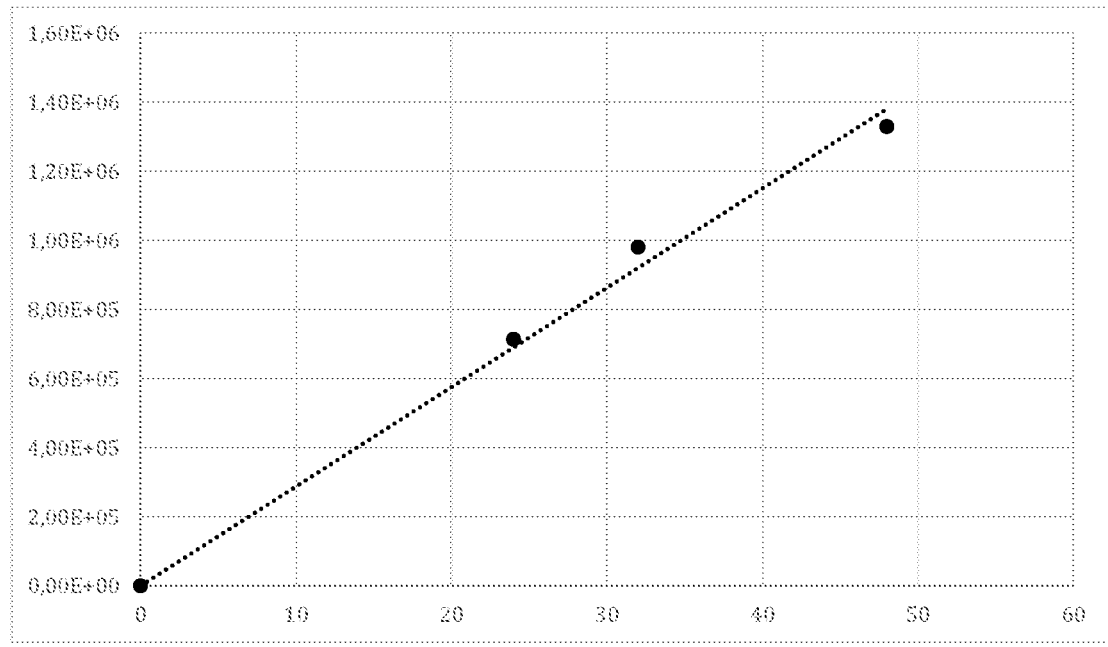
FIG. 2 is a graph representing the absorbance of several solutions of gentamicin at different concentrations prepared from dissolving saccharose beads grafted with gentamicin on the surface.

Example 3—Gentamycin Range (FIG. 2)

To prepare the solution that will be deposited on the beads, 10 mg/mL gentamicin will be diluted 5000. 100 μL of the stock solution is added to 900 μL of H₂O. 100 μL of the solution generated is added to 900 μL of H₂O. 500 μL of the solution generated is added to 500 μL of H₂O to obtain a 100 μg/mL solution. 40 μL of the 100 μg/mL solution is added to 960 μL of methanol. The grafting of gentamicin onto the 3 mm saccharose beads is performed as described in Example 1.

A concentration range is prepared by taking up a bead in:
1 mL of a methanol/H$_2$O solution (70%/30%, v/v)
750 μL of a methanol/H$_2$O solution (70%/30%, v/v)
500 μL of a methanol/H$_2$O solution (70%/30%, v/v)
A 20 μL volume of the sample obtained is injected and analysed according to the following conditions:
Agilent 1290 chromatographic system (Les Ulys, France)
Xbridge Hilic amide column 2.1 mm*100, 3.5 μm WATERS Column
Solvent A: H$_2$O+0.1% formic acid
Solvent B: ACN+0.1% formic acid
Liquid chromatography gradient as follows:

| min | Flow (μL/min) | Solvent A | Solvent B |
| --- | --- | --- | --- |
| 0 | 300 | 45 | 55 |
| 1 | 300 | 45 | 55 |
| 4 | 300 | 50 | 15 |
| 4.1 | 300 | 95 | 5 |
| 7 | 300 | 95 | 95 |
| 7.1 | 300 | 35 | 65 |
| 11 | 300 | 35 | 65 |

The eluate leaving the chromatographic column can also be injected directly into the ionization source of a Sciex QTRAP® 5500 mass spectrometer (Foster City, USA). The following machine parameters are used:
Scan type: MRM
Polarity: Positive
Ionization source: Turbo V (Sciex)
Precursor: 478.4
Ion fragment: 322.4
Ion fragment: 160.0
Setting Q1: Filtering with unit resolution
Setting Q3: Filtering with unit resolution
Cone voltage: 5500 V
Source temperature: 500.00° C.
Nebulizer gas: 50.00 psi
Heating gas: 40.00 psi
Curtain gas: 50.00 psi
The results are shown in FIG. 2.

Figure 3A:
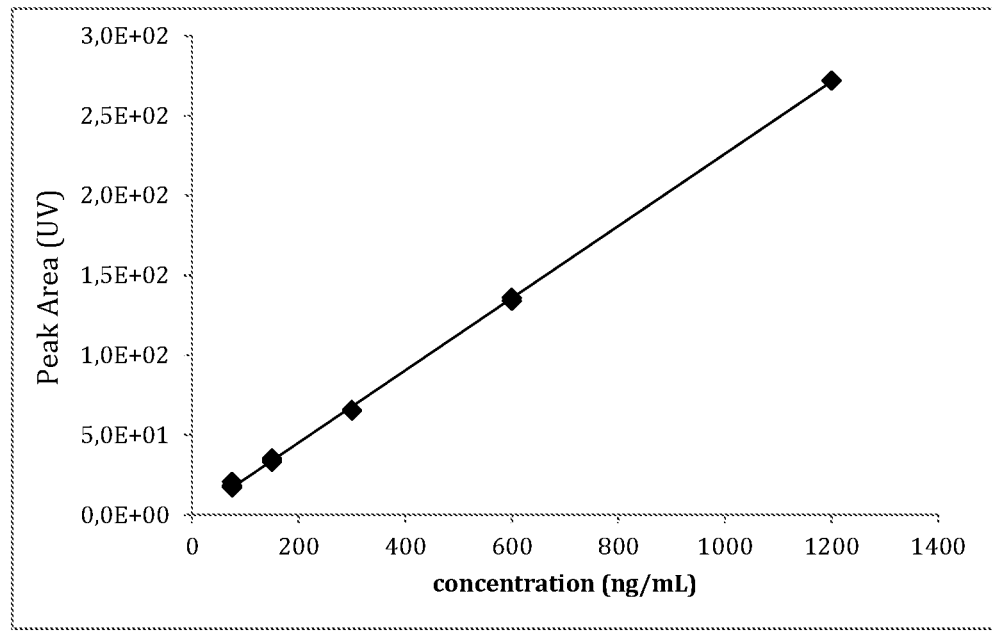
FIGS. 3A and 3B are graphs representing the absorbance of several solutions at different concentrations prepared from dissolving saccharose beads grafted with peptide GDVAFVK. Graphs 3A and 3B have been recorded 2 weeks apart.
Figure 3B:
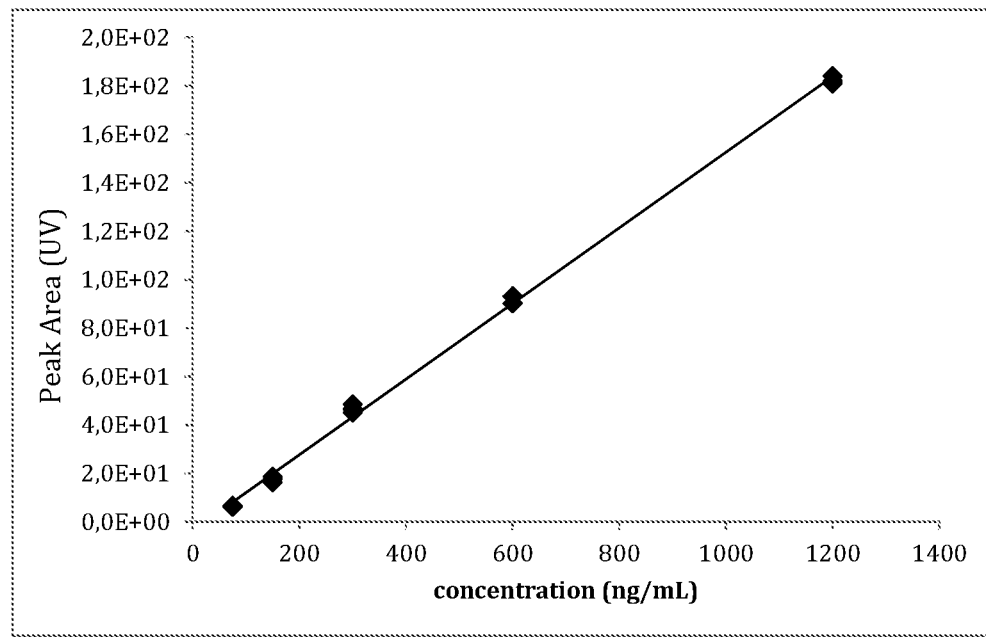

Example 4—Ranges Prepared at Two-Week Intervals with Beads Produced from Stock Solutions of Different Concentrations (FIGS. 3A and 3B)

A stock solution of peptide is prepared by taking up 200 μg of peptide GDVAFVK lysine (K)-labelled with heavy isotopes 13C and 15N in 1 mL of a methanol 0.5% formic acid solution. 350 μL of the stock solution is diluted in 350 μL of methanol 0.5% formic acid to obtain a 100 μg/mL stock solution. 350 μL of the 100 μg/mL stock solution is diluted in 350 μL of methanol 0.5% formic acid to obtain a 50 μg/mL stock solution. 350 μL of the 50 μg/mL stock solution is diluted in 350 μL of methanol 0.5% formic acid to obtain a 25 μg/mL stock solution.
350 μL of the 25 μg/mL stock solution is diluted in 350 μL of methanol 0.5% formic acid to obtain a 12.5 μg/mL stock solution. 350 μL of the 12.5 μg/mL stock solution is diluted in 350 μL of methanol 0.5% formic acid to obtain a 6.25 μg/mL stock solution.
Each of the stock solutions is used for grafting onto sucrose beads according to the protocol cited in Example 1.
Each of the beads grafted with amounts of peptide GDVAFVK ranging from 1.2 μg to 12.5 ng is taken up in 500 μL of a 95% H$_2$O, 5% ACN, 0.5% formic acid solution and solubilized for 2 minutes.
A 40 μL volume of each sample obtained is injected and analysed according to the following conditions:
Agilent 1290 chromatographic system (Les Ulys, France)
Phenomenex Aeris peptide C18 column, 2.1 mm internal diameter, 100 mm in length, 3.6 mm particle size
Solvent A: H$_2$O+0.1% formic acid
Solvent B: ACN+0.1% formic acid
Liquid chromatography gradient as follows

| min | Flow (μL/min) | Solvent A | Solvent B |
| --- | --- | --- | --- |
| 0 | 300 | 95 | 5 |
| 1 | 300 | 95 | 5 |
| 8 | 300 | 50 | 50 |
| 8.1 | 300 | 5 | 95 |
| 12 | 300 | 5 | 95 |
| 12.1 | 300 | 95 | 5 |
| 15 | 300 | 95 | 5 |

The eluate leaving the chromatographic column is injected directly into an Agilent 1290 diode array detector. UV absorption is measured at a wavelength of 205 nm.
The results shown in FIGS. 3A and 3B confirm the reproducibility of the method according to the invention.

Example 5—Quantification of Apolipoprotein E in Plasma by Peptide LGPLVEQGR Valine (V)-Labelled with 13C and 15N The polymer beads are prepared from a 1 μg/mL stock solution of peptide LGPLVEQGR according to the protocol described in Example 1.
Enzymatic digestion of plasma according to the following protocol:
1 mL of plasma diluted in 4 mL of 8 M urea
550 μL of 150 mM DTT
1700 μL of 150 mM IAA
30 mL of 50 mM ammonium bicarbonate (pH 8)
1 mL of 2 mg/mL trypsin in 50 mM ammonium bicarbonate (pH 8).
1 mL of H$_2$O+0.5% FA is added to 10 μL of hydrolysed plasma
A polymer bead grafted with 6 ng of peptide LGPLVEQGR is added.
Desalting and concentration of the samples by solid phase extraction according to the following protocol:
Equilibration of the Waters Oasis HLB columns with 1 mL of methanol then 1 mL of H$_2$O/0.1% formic acid.
Deposition of the sample which flows by gravity
Wash with 1 mL of H$_2$O/0.1% formic acid.
Elution with 1 mL of 80% methanol in an H$_2$O/0.1% formic acid mixture
Dry evaporation and taking up in 200 μL of a 95% H$_2$O, 5% ACN, 0.5% formic acid solution.
A 20 μL volume of the sample obtained is injected and analysed according to the following conditions:
Agilent 1290 chromatographic system (Les Ulys, France)
Phenomenex Aeris peptide C18 column, 2.1 mm internal diameter, 100 mm in length, 3.6 mm particle size
Solvent A: H$_2$O+0.1% formic acid
Solvent B: ACN+0.1% formic acid Liquid chromatography gradient as follows

| min | Flow (μL/min) | Solvent A | Solvent B |
|---|---|---|---|
| 0 | 300 | 95 | 5 |
| 1 | 300 | 95 | 5 |
| 8 | 300 | 50 | 50 |
| 8.1 | 300 | 5 | 95 |
| 10 | 300 | 5 | 95 |
| 10.1 | 300 | 95 | 5 |
| 12 | 300 | 95 | 5 |

The eluate leaving the chromatographic column can also be injected directly into the ionization source of a Sciex QTRAP® 5500 mass spectrometer (Foster City, USA). The following machine parameters are used:
Scan type: MRM
Polarity: Positive
Ionization source: Turbo V (Sciex)
Setting Q1: Filtering with unit resolution
Setting Q3: Filtering with unit resolution
Cone voltage: 5500 V
Source temperature: 500.00° C.
Nebulizer gas: 50.00 psi
Heating gas: 40.00 psi
Curtain gas: 50.00 psi The mass values and the optical path parameters are as follows:

| ID | Q1/Q3 | time | DP | EP | CE | CXP |
|---|---|---|---|---|---|---|
| APOEHUMAN_LGPLVEQGR_+2y5_light | 484.8/855.5 | 100 ms | 66.5 | 10 | 26.3 | 13 |
| APOEHUMAN_LGPLVEQGR_+2y6_light | 484.8/798.4 | 100 ms | 66.5 | 10 | 26.3 | 13 |
| APOEHUMAN_LGPLVEQGR_+2y7_light | 484.8/701.4 | 100 ms | 66.5 | 10 | 26.3 | 13 |
| APOEHUMAN_LGPLVEQGR_+2y7+2_light | 484.8/588.3 | 100 ms | 66.5 | 10 | 26.3 | 13 |
| APOEHUMAN_LGPLVEQGR_+2y8_light | 484.8/399.7 | 100 ms | 66.5 | 10 | 26.3 | 13 |
| APOEHUMAN_LGPLVEQGR-heavy_+2y5_heavy | 487.8/861.5 | 100 ms | 66.5 | 10 | 26.3 | 13 |
| APOEHUMAN_LGPLVEQGR-heavy_+2y6_heavy | 487.8/804.5 | 100 ms | 66.5 | 10 | 26.3 | 13 |
| APOEHUMAN_LGPLVEQGR-heavy_+2y7_heavy | 487.8/707.4 | 100 ms | 66.5 | 10 | 26.3 | 13 |

Example 6—Preservation of Enzymatic Activity

Beads grafted with trypsin were prepared from a 1 mg/mL stock solution of trypsin according to the protocol described in Example 1.

The trypsin activity of the proteins after dissolution of the beads in an appropriate buffer is observed by hydrolysis of albumin according to the method for identifying peptides resulting from trypsin hydrolysis by mass spectrometry. The peptides resulting from trypsin hydrolysis are specifically monitored to determine their presence in the samples.

The results obtained show that trypsin activity is preserved after grafting onto the beads, the process according to the invention having no protein denaturing action. A comparison with the activity of non-grafted trypsin shows similar or even higher activity with the trypsin solution prepared from the grafted beads.

These results confirm that it is possible to prepare beads of predetermined amounts of proteins or enzymes, making it possible to facilitate the preparation of solutions having a determined proportion of proteins, in particular for preparing enzyme solutions.

REFERENCES

EP 1 456 227
WO 2010/035504
WO 2014/066284

The invention claimed is:

1. A process for preparing an aqueous solution of at least ten different products to be dissolved, wherein the process comprises dissolving in the solvent of the aqueous solution one or more soluble beads, the one or more soluble beads having a surface, wherein the at least ten products to be dissolved are present at the surface of each of the one or more soluble beads and being grafted thereon, wherein the beads are calibrated with a homogeneous diameter ranging from 1 to 4 mm.

2. The process as claimed in claim 1, wherein the solvent contains water and the beads consist of one or more water soluble compounds chosen among sugars, polysaccharides, hydroxycarboxylic acids, and mixtures thereof.

3. The process as claimed in claim 2, wherein the beads consist of one or more water soluble compounds chosen among sucrose, lactose, alginates and lactic acid.

4. The process as claimed in claim 1, wherein the amount of the at least ten products to be dissolved and grafted onto each bead is predetermined, from 1 picogram to 100 micrograms per bead.

5. The process as claimed in claim 1, wherein the at least ten products to be dissolved are chosen among peptides, proteins and small molecules, optionally isotopically labelled, deuterated or contain modifications selected among phosphorylation, oxidation and carbamidomethylation.

6. The process as claimed in claim 1, wherein the solution prepared is suitable for use in spectrometric analysis method.

7. A set of soluble beads carrying at least ten different products to be analysed grafted onto the surface of each of the soluble beads, wherein the beads each have a predetermined amount of the at least ten different products grafted onto their substantially equal surface.

8. The set of beads as claimed in claim 7, wherein the beads are packaged in the same package allowing controlled release of the number of beads.

9. A range of products to be analysed wherein the range comprises at least two sets of beads as claimed in claim 7, each set having a predetermined amount of adsorbed products different from the other sets.

10. The range as claimed in claim 9, wherein the predetermined amounts of each set are separated by a predetermined factor.

11. A process for preparing soluble beads carrying at least ten different products to be analysed grafted onto the surface of each of the soluble beads, comprising a first step of impregnating polymer beads with a solution containing the at least one product of the ten products to be dissolved in order to allow the grafting of said products of the beads, then a step of drying the grafted beads obtained, wherein the beads are calibrated with a homogeneous diameter and the amount of product grafted onto each bead is predetermine, from 1 picogram to 100 micrograms per bead.

12. The process as claimed in claim 11, wherein the impregnation and/or the drying is carried out under controlled atmosphere.

13. The process as claimed in claim 11, wherein the impregnation and drying cycle is repeated several times.

14. The set of beads as claimed in claim 7, wherein the beads are calibrated with a homogeneous diameter.

15. The set of beads as claimed in claim 14, wherein the diameter of the beads ranges from 1 to 4 mm.

16. The set of beads of at least ten different products to be dissolved as claimed in claim 7, wherein the solvent contains water and the beads consists of one or more water-soluble compounds chosen among sugars, polysaccharides, hydroxycarboxylic acids, and mixtures thereof.

17. The set of beads as claimed in claim 16, wherein the water-soluble compound is chosen among sucrose, lactose, alginates and lactic acid.

18. The set of beads as claimed in claim 7, wherein the amount of product grafted onto each bead is predetermined, from 1 picogram to 100 micrograms per bead.

19. The set of beads as claimed in claim 7, wherein the product is chosen among peptides, proteins and small molecules, optionally isotopically labelled, deuterated or contain modifications selected among phosphorylation, oxidation and carbamidomethylation.

20. The set of beads as claimed in claim 7, wherein the solution prepared is suitable for use in a spectrometric analysis method.

21. The process according to claim 1, wherein the soluble bead comprises at least ten different products to be dissolved grafted onto its surface.

\* \* \* \* \*

SEQUENCE LISTING

<160> NUMBER OF SEQ ID NOS: 160

<210> SEQ ID NO 1
<211> LENGTH: 9
<212> TYPE: PRT
<213> ORGANISM: Artificial sequence
<220> FEATURE:
<223> OTHER INFORMATION: Peptide

```
<400> SEQUENCE: 1

Glu Gly Val Leu Tyr Val Gly Ser Lys
1               5

<210> SEQ ID NO 2
<211> LENGTH: 9
<212> TYPE: PRT
<213> ORGANISM: Artificial sequence
<220> FEATURE:
<223> OTHER INFORMATION: peptide

<400> SEQUENCE: 2

Glu Gly Val Val Ala Ala Ala Glu Lys
1               5

<210> SEQ ID NO 3
<211> LENGTH: 13
<212> TYPE: PRT
<213> ORGANISM: Artificial sequence
<220> FEATURE:
<223> OTHER INFORMATION: peptide

<400> SEQUENCE: 3

Glu Gly Val Val His Gly Val Thr Thr Val Ala Glu Lys
1               5                   10

<210> SEQ ID NO 4
<211> LENGTH: 20
<212> TYPE: PRT
<213> ORGANISM: Artificial sequence
<220> FEATURE:
<223> OTHER INFORMATION: peptide

<400> SEQUENCE: 4

Glu Gln Val Thr Asn Val Gly Gly Ala Val Val Thr Gly Val Thr Ala
1               5                   10                  15

Val Ala Gln Lys
            20

<210> SEQ ID NO 5
<211> LENGTH: 9
<212> TYPE: PRT
<213> ORGANISM: Artificial sequence
<220> FEATURE:
<223> OTHER INFORMATION: peptide

<400> SEQUENCE: 5

Gln Gly Val Ala Glu Ala Ala Gly Lys
1               5

<210> SEQ ID NO 6
<211> LENGTH: 16
<212> TYPE: PRT
<213> ORGANISM: Artificial sequence
<220> FEATURE:
<223> OTHER INFORMATION: peptide

<400> SEQUENCE: 6

Thr Val Glu Gly Ala Gly Asn Ile Ala Ala Ala Thr Gly Phe Val Lys
1               5                   10                  15

<210> SEQ ID NO 7
<211> LENGTH: 26
<212> TYPE: PRT
<213> ORGANISM: Artificial sequence
```

```
<220> FEATURE:
<223> OTHER INFORMATION: peptide

<400> SEQUENCE: 7

Ala Glu Glu Ala Gly Ile Gly Asp Thr Pro Asn Gln Glu Asp Gln Ala
1               5                   10                  15

Ala Gly His Val Thr Pro His Gln Ala Arg
            20                  25

<210> SEQ ID NO 8
<211> LENGTH: 24
<212> TYPE: PRT
<213> ORGANISM: Artificial sequence
<220> FEATURE:
<223> OTHER INFORMATION: peptide

<400> SEQUENCE: 8

Ala Glu Glu Ala Gly Ile Gly Asp Thr Pro Asn Gln Glu Asp Gln Ala
1               5                   10                  15

Ala Gly His Val Thr Gln Ala Arg
            20

<210> SEQ ID NO 9
<211> LENGTH: 26
<212> TYPE: PRT
<213> ORGANISM: Artificial sequence
<220> FEATURE:
<223> OTHER INFORMATION: peptide

<400> SEQUENCE: 9

Ala Glu Glu Ala Gly Ile Gly Asp Thr Pro Ser Leu Glu Asp Glu Ala
1               5                   10                  15

Ala Gly His Val Thr Pro His Gln Ala Arg
            20                  25

<210> SEQ ID NO 10
<211> LENGTH: 24
<212> TYPE: PRT
<213> ORGANISM: Artificial sequence
<220> FEATURE:
<223> OTHER INFORMATION: peptide

<400> SEQUENCE: 10

Ala Glu Glu Ala Gly Ile Gly Asp Thr Pro Ser Leu Glu Asp Glu Ala
1               5                   10                  15

Ala Gly His Val Thr Gln Ala Arg
            20

<210> SEQ ID NO 11
<211> LENGTH: 22
<212> TYPE: PRT
<213> ORGANISM: Artificial sequence
<220> FEATURE:
<223> OTHER INFORMATION: peptide

<400> SEQUENCE: 11

Cys Cys Ala Met Gly Ser Leu Gly Asn Ile His His Lys Pro Gly Gly
1               5                   10                  15

Gly Gln Val Glu Val Lys
            20

<210> SEQ ID NO 12
<211> LENGTH: 8
<212> TYPE: PRT
```

```
<213> ORGANISM: Artificial sequence
<220> FEATURE:
<223> OTHER INFORMATION: peptide

<400> SEQUENCE: 12

Asp Arg Thr Gly Asn Asp Glu Lys
1               5

<210> SEQ ID NO 13
<211> LENGTH: 25
<212> TYPE: PRT
<213> ORGANISM: Artificial sequence
<220> FEATURE:
<223> OTHER INFORMATION: peptide

<400> SEQUENCE: 13

Glu Ser Pro His Pro Leu Gln Thr Pro Thr Glu Asp Gly Ser Glu Glu
1               5                   10                  15

Pro Gly Ser Glu Thr Ser Asp Ala Lys
            20                  25

<210> SEQ ID NO 14
<211> LENGTH: 25
<212> TYPE: PRT
<213> ORGANISM: Artificial sequence
<220> FEATURE:
<223> OTHER INFORMATION: peptide

<400> SEQUENCE: 14

Glu Ser Pro His Pro Pro Gln Pro Pro Ala Asp Asp Gly Ala Glu Glu
1               5                   10                  15

Pro Gly Ser Glu Thr Ser Asp Ala Lys
            20                  25

<210> SEQ ID NO 15
<211> LENGTH: 23
<212> TYPE: PRT
<213> ORGANISM: Artificial sequence
<220> FEATURE:
<223> OTHER INFORMATION: peptide

<400> SEQUENCE: 15

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 16
<211> LENGTH: 23
<212> TYPE: PRT
<213> ORGANISM: Artificial sequence
<220> FEATURE:
<223> OTHER INFORMATION: peptide

<400> SEQUENCE: 16

Glu Ser Pro Pro Gln Pro Pro Ala Asp Asp Gly Ala Glu Glu Pro Gly
1               5                   10                  15

Ser Glu Thr Ser Asp Ala Lys
            20

<210> SEQ ID NO 17
<211> LENGTH: 8
<212> TYPE: PRT
<213> ORGANISM: Artificial sequence
<220> FEATURE:
```

```
<223> OTHER INFORMATION: peptide

<400> SEQUENCE: 17

Gly Ala Ala Pro Pro Gly Gln Lys
1               5

<210> SEQ ID NO 18
<211> LENGTH: 8
<212> TYPE: PRT
<213> ORGANISM: Artificial sequence
<220> FEATURE:
<223> OTHER INFORMATION: peptide

<400> SEQUENCE: 18

Gly Ala Ala Ser Pro Ala Gln Lys
1               5

<210> SEQ ID NO 19
<211> LENGTH: 32
<212> TYPE: PRT
<213> ORGANISM: Artificial sequence
<220> FEATURE:
<223> OTHER INFORMATION: peptide

<400> SEQUENCE: 19

His Leu Ser Asn Val Ser Ser Thr Gly Ser Ile Asp Met Val Asp Ser
1               5                   10                  15

Pro Gln Leu Ala Thr Leu Ala Asp Glu Val Ser Ala Ser Leu Ala Lys
            20                  25                  30

<210> SEQ ID NO 20
<211> LENGTH: 19
<212> TYPE: PRT
<213> ORGANISM: Artificial sequence
<220> FEATURE:
<223> OTHER INFORMATION: peptide

<400> SEQUENCE: 20

His Val Leu Gly Gly Gly Ser Val Gln Ile Val Tyr Lys Pro Val Asp
1               5                   10                  15

Leu Ser Lys

<210> SEQ ID NO 21
<211> LENGTH: 19
<212> TYPE: PRT
<213> ORGANISM: Artificial sequence
<220> FEATURE:
<223> OTHER INFORMATION: peptide

<400> SEQUENCE: 21

His Val Pro Gly Gly Gly Ser Val Gln Ile Val Tyr Lys Pro Val Asp
1               5                   10                  15

Leu Ser Lys

<210> SEQ ID NO 22
<211> LENGTH: 13
<212> TYPE: PRT
<213> ORGANISM: Artificial sequence
<220> FEATURE:
<223> OTHER INFORMATION: peptide

<400> SEQUENCE: 22

Ile Ala Thr Pro Arg Gly Ala Ala Pro Pro Gly Gln Lys
1               5                   10
```

```
<210> SEQ ID NO 23
<211> LENGTH: 12
<212> TYPE: PRT
<213> ORGANISM: Artificial sequence
<220> FEATURE:
<223> OTHER INFORMATION: peptide

<400> SEQUENCE: 23

Thr Phe Asp Pro Tyr Tyr Ala Val Ala Leu Val Lys
1               5                   10

<210> SEQ ID NO 24
<211> LENGTH: 12
<212> TYPE: PRT
<213> ORGANISM: Artificial sequence
<220> FEATURE:
<223> OTHER INFORMATION: peptide

<400> SEQUENCE: 24

Phe Thr Asp Pro Val Asn Ile Ile Ser Val Tyr Lys
1               5                   10

<210> SEQ ID NO 25
<211> LENGTH: 17
<212> TYPE: PRT
<213> ORGANISM: Artificial sequence
<220> FEATURE:
<223> OTHER INFORMATION: peptide

<400> SEQUENCE: 25

Leu Gly Asp Pro Leu Gly Ala Asp Val Ala Gln Val Thr Gly Ala Leu
1               5                   10                  15

Arg

<210> SEQ ID NO 26
<211> LENGTH: 12
<212> TYPE: PRT
<213> ORGANISM: Artificial sequence
<220> FEATURE:
<223> OTHER INFORMATION: peptide

<400> SEQUENCE: 26

Gly Ile Asp Pro Glu Ala Val Leu Ala Asp Leu Arg
1               5                   10

<210> SEQ ID NO 27
<211> LENGTH: 15
<212> TYPE: PRT
<213> ORGANISM: Artificial sequence
<220> FEATURE:
<223> OTHER INFORMATION: peptide

<400> SEQUENCE: 27

Tyr Asp Pro Leu Val Val Phe Ser His Gly Leu Gly Ala Phe Arg
1               5                   10                  15

<210> SEQ ID NO 28
<211> LENGTH: 12
<212> TYPE: PRT
<213> ORGANISM: Artificial sequence
<220> FEATURE:
<223> OTHER INFORMATION: peptide

<400> SEQUENCE: 28

Gln Asp Pro Asn Glu Ile Leu Ile Phe Trp Ser Lys
1               5                   10
```

<210> SEQ ID NO 29
<211> LENGTH: 22
<212> TYPE: PRT
<213> ORGANISM: Artificial sequence
<220> FEATURE:
<223> OTHER INFORMATION: peptide

<400> SEQUENCE: 29

Glu Gln Asp Pro Val Thr Asn Val Gly Gly Ala Val Val Thr Gly Val
1               5                   10                  15

Thr Ala Val Ala Gln Lys
            20

<210> SEQ ID NO 30
<211> LENGTH: 12
<212> TYPE: PRT
<213> ORGANISM: Artificial sequence
<220> FEATURE:
<223> OTHER INFORMATION: peptide

<400> SEQUENCE: 30

Ile Asp Pro Gly Ser Ser Asp Gly Ser Ser Ser Arg
1               5                   10

<210> SEQ ID NO 31
<211> LENGTH: 11
<212> TYPE: PRT
<213> ORGANISM: Artificial sequence
<220> FEATURE:
<223> OTHER INFORMATION: peptide

<400> SEQUENCE: 31

Glu Gly Asp Pro Val Val Ala Ala Ala Glu Lys
1               5                   10

<210> SEQ ID NO 32
<211> LENGTH: 11
<212> TYPE: PRT
<213> ORGANISM: Artificial sequence
<220> FEATURE:
<223> OTHER INFORMATION: peptide

<400> SEQUENCE: 32

Glu Ala Asp Pro Asn Tyr Ile Gly Ser Asp Lys
1               5                   10

<210> SEQ ID NO 33
<211> LENGTH: 13
<212> TYPE: PRT
<213> ORGANISM: Artificial sequence
<220> FEATURE:
<223> OTHER INFORMATION: peptide

<400> SEQUENCE: 33

Ser Gln Asp Pro Thr Val Leu Gln Asn Thr Gly Gly Arg
1               5                   10

<210> SEQ ID NO 34
<211> LENGTH: 11
<212> TYPE: PRT
<213> ORGANISM: Artificial sequence
<220> FEATURE:
<223> OTHER INFORMATION: peptide

<400> SEQUENCE: 34

Ser Gly Asp Pro Gly Val Cys Leu Asn Cys Arg
1               5                   10

<210> SEQ ID NO 35
<211> LENGTH: 11
<212> TYPE: PRT
<213> ORGANISM: Artificial sequence
<220> FEATURE:
<223> OTHER INFORMATION: peptide

<400> SEQUENCE: 35

Ala Thr Asp Pro Phe Asn Pro Ala Gln Asp Lys
1               5                   10

<210> SEQ ID NO 36
<211> LENGTH: 11
<212> TYPE: PRT
<213> ORGANISM: Artificial sequence
<220> FEATURE:
<223> OTHER INFORMATION: peptide

<400> SEQUENCE: 36

Ala Asn Asp Pro Ile Gly Ala Thr Leu Asn Arg
1               5                   10

<210> SEQ ID NO 37
<211> LENGTH: 11
<212> TYPE: PRT
<213> ORGANISM: Artificial sequence
<220> FEATURE:
<223> OTHER INFORMATION: peptide

<400> SEQUENCE: 37

Leu Tyr Tyr Asp Pro Ser Gln Asp Asn Asp Arg
1               5                   10

<210> SEQ ID NO 38
<211> LENGTH: 9
<212> TYPE: PRT
<213> ORGANISM: Artificial sequence
<220> FEATURE:
<223> OTHER INFORMATION: peptide

<400> SEQUENCE: 38

Ser Asp Pro Ile Ala Pro Cys Ile Lys
1               5

<210> SEQ ID NO 39
<211> LENGTH: 11
<212> TYPE: PRT
<213> ORGANISM: Artificial sequence
<220> FEATURE:
<223> OTHER INFORMATION: peptide

<400> SEQUENCE: 39

Ser Leu Ala Asp Pro Ala Val Val Thr Gly Lys
1               5                   10

<210> SEQ ID NO 40
<211> LENGTH: 7
<212> TYPE: PRT
<213> ORGANISM: Artificial sequence
<220> FEATURE:
<223> OTHER INFORMATION: peptide

<400> SEQUENCE: 40

Thr Leu Asp Pro Phe Ser Arg

```
<210> SEQ ID NO 41
<211> LENGTH: 18
<212> TYPE: PRT
<213> ORGANISM: Artificial sequence
<220> FEATURE:
<223> OTHER INFORMATION: peptide

<400> SEQUENCE: 41

Leu His Asp Pro Thr Phe Gly Asp Glu Asn Glu Asp Asp Ser Glu Leu
1               5                   10                  15

Ala Arg

<210> SEQ ID NO 42
<211> LENGTH: 10
<212> TYPE: PRT
<213> ORGANISM: Artificial sequence
<220> FEATURE:
<223> OTHER INFORMATION: peptide

<400> SEQUENCE: 42

Ala Ser Asp Pro Tyr Leu Asp Cys Ile Lys
1               5                   10

<210> SEQ ID NO 43
<211> LENGTH: 18
<212> TYPE: PRT
<213> ORGANISM: Artificial sequence
<220> FEATURE:
<223> OTHER INFORMATION: peptide

<400> SEQUENCE: 43

Ile Gly Asp Pro Ser Leu Asp Asn Ile Thr His Val Pro Gly Gly Gly
1               5                   10                  15

Asn Lys

<210> SEQ ID NO 44
<211> LENGTH: 14
<212> TYPE: PRT
<213> ORGANISM: Artificial sequence
<220> FEATURE:
<223> OTHER INFORMATION: peptide

<400> SEQUENCE: 44

Ala Asp Pro Ala Ala Thr Val Val Asp Val Asp Glu Val Arg
1               5                   10

<210> SEQ ID NO 45
<211> LENGTH: 6
<212> TYPE: PRT
<213> ORGANISM: Artificial sequence
<220> FEATURE:
<223> OTHER INFORMATION: peptide

<400> SEQUENCE: 45

Val Gln Ile Ile Asn Lys
1               5

<210> SEQ ID NO 46
<211> LENGTH: 14
<212> TYPE: PRT
<213> ORGANISM: Artificial sequence
<220> FEATURE:
<223> OTHER INFORMATION: peptide
```

```
<400> SEQUENCE: 46

Val Gln Ile Val Tyr Pro His Lys Pro Val Asp Leu Ser Lys
1               5                   10

<210> SEQ ID NO 47
<211> LENGTH: 15
<212> TYPE: PRT
<213> ORGANISM: Artificial sequence
<220> FEATURE:
<223> OTHER INFORMATION: peptide

<400> SEQUENCE: 47

Ala Val Phe Val Asp Leu Glu Pro Thr Val Ile Asp Glu Val Arg
1               5                   10                  15

<210> SEQ ID NO 48
<211> LENGTH: 18
<212> TYPE: PRT
<213> ORGANISM: Artificial sequence
<220> FEATURE:
<223> OTHER INFORMATION: peptide

<400> SEQUENCE: 48

Val Gly Ile Asn Tyr Gln Pro Pro Thr Val Val Pro Gly Gly Asp Leu
1               5                   10                  15

Ala Lys

<210> SEQ ID NO 49
<211> LENGTH: 18
<212> TYPE: PRT
<213> ORGANISM: Artificial sequence
<220> FEATURE:
<223> OTHER INFORMATION: peptide

<400> SEQUENCE: 49

Val Ala Pro Glu Glu His Pro Val Leu Leu Thr Glu Ala Pro Leu Asn
1               5                   10                  15

Pro Lys

<210> SEQ ID NO 50
<211> LENGTH: 10
<212> TYPE: PRT
<213> ORGANISM: Artificial sequence
<220> FEATURE:
<223> OTHER INFORMATION: peptide

<400> SEQUENCE: 50

Asp Val Asn Ala Ala Ile Ala Ala Ile Lys
1               5                   10

<210> SEQ ID NO 51
<211> LENGTH: 9
<212> TYPE: PRT
<213> ORGANISM: Artificial sequence
<220> FEATURE:
<223> OTHER INFORMATION: peptide

<400> SEQUENCE: 51

Glu Ile Ile Asp Pro Val Leu Asp Arg
1               5

<210> SEQ ID NO 52
<211> LENGTH: 11
<212> TYPE: PRT
<213> ORGANISM: Artificial sequence
```

```
<220> FEATURE:
<223> OTHER INFORMATION: peptide

<400> SEQUENCE: 52

Asp Ser Tyr Val Gly Asp Glu Ala Gln Ser Lys
1               5                   10

<210> SEQ ID NO 53
<211> LENGTH: 11
<212> TYPE: PRT
<213> ORGANISM: Artificial sequence
<220> FEATURE:
<223> OTHER INFORMATION: peptide

<400> SEQUENCE: 53

Ala Val Phe Pro Ser Ile Val Gly Arg Pro Arg
1               5                   10

<210> SEQ ID NO 54
<211> LENGTH: 9
<212> TYPE: PRT
<213> ORGANISM: Artificial sequence
<220> FEATURE:
<223> OTHER INFORMATION: peptide

<400> SEQUENCE: 54

Gly Ile Ala Pro Leu Gln Leu Gly Lys
1               5

<210> SEQ ID NO 55
<211> LENGTH: 16
<212> TYPE: PRT
<213> ORGANISM: Artificial sequence
<220> FEATURE:
<223> OTHER INFORMATION: peptide

<400> SEQUENCE: 55

Leu His Thr Phe Gly Asp Glu Asn Glu Asp Asp Ser Glu Leu Ala Arg
1               5                   10                  15

<210> SEQ ID NO 56
<211> LENGTH: 9
<212> TYPE: PRT
<213> ORGANISM: Artificial sequence
<220> FEATURE:
<223> OTHER INFORMATION: peptide

<400> SEQUENCE: 56

Ser Gly Gly Val Cys Leu Asn Cys Arg
1               5

<210> SEQ ID NO 57
<211> LENGTH: 8
<212> TYPE: PRT
<213> ORGANISM: Artificial sequence
<220> FEATURE:
<223> OTHER INFORMATION: peptide

<400> SEQUENCE: 57

Ser Pro Ile Ala Pro Cys Ile Lys
1               5

<210> SEQ ID NO 58
<211> LENGTH: 8
<212> TYPE: PRT
<213> ORGANISM: Artificial sequence
<220> FEATURE:
```

<223> OTHER INFORMATION: peptide

<400> SEQUENCE: 58

Ser Ser Leu Val Ile Gln Trp Arg
1               5

<210> SEQ ID NO 59
<211> LENGTH: 14
<212> TYPE: PRT
<213> ORGANISM: Artificial sequence
<220> FEATURE:
<223> OTHER INFORMATION: peptide

<400> SEQUENCE: 59

Phe Asp Pro Val His Ala Ala Leu Val Trp Gly Pro Glu Lys
1               5                   10

<210> SEQ ID NO 60
<211> LENGTH: 10
<212> TYPE: PRT
<213> ORGANISM: Artificial sequence
<220> FEATURE:
<223> OTHER INFORMATION: peptide

<400> SEQUENCE: 60

Ser Tyr Asp Pro Tyr Trp Ile Gly Ile Arg
1               5                   10

<210> SEQ ID NO 61
<211> LENGTH: 13
<212> TYPE: PRT
<213> ORGANISM: Artificial sequence
<220> FEATURE:
<223> OTHER INFORMATION: peptide

<400> SEQUENCE: 61

Ile Ala Thr Pro Arg Gly Ala Ala Ser Pro Ala Gln Lys
1               5                   10

<210> SEQ ID NO 62
<211> LENGTH: 18
<212> TYPE: PRT
<213> ORGANISM: Artificial sequence
<220> FEATURE:
<223> OTHER INFORMATION: peptide

<400> SEQUENCE: 62

Ile Gly Ser Pro His Leu Asp Asn Ile Thr His Val Pro Gly Gly Gly
1               5                   10                  15

Asn Lys

<210> SEQ ID NO 63
<211> LENGTH: 10
<212> TYPE: PRT
<213> ORGANISM: Artificial sequence
<220> FEATURE:
<223> OTHER INFORMATION: peptide

<400> SEQUENCE: 63

Ile Gly Ser Pro His Thr Glu Asn Leu Lys
1               5                   10

<210> SEQ ID NO 64
<211> LENGTH: 16
<212> TYPE: PRT
<213> ORGANISM: Artificial sequence -continued

```
<220> FEATURE:
<223> OTHER INFORMATION: peptide

<400> SEQUENCE: 64

Ile Gly Ser Leu Asp Asn Ile Thr His Val Pro Gly Gly Asn Lys
1               5                   10                  15

<210> SEQ ID NO 65
<211> LENGTH: 8
<212> TYPE: PRT
<213> ORGANISM: Artificial sequence
<220> FEATURE:
<223> OTHER INFORMATION: peptide

<400> SEQUENCE: 65

Ile Gly Ser Thr Glu Asn Leu Lys
1               5

<210> SEQ ID NO 66
<211> LENGTH: 11
<212> TYPE: PRT
<213> ORGANISM: Artificial sequence
<220> FEATURE:
<223> OTHER INFORMATION: peptide

<400> SEQUENCE: 66

Leu Asp Leu Ser Asn Val Gln Ser Pro His Lys
1               5                   10

<210> SEQ ID NO 67
<211> LENGTH: 9
<212> TYPE: PRT
<213> ORGANISM: Artificial sequence
<220> FEATURE:
<223> OTHER INFORMATION: peptide

<400> SEQUENCE: 67

Leu Asp Leu Ser Asn Val Gln Ser Lys
1               5

<210> SEQ ID NO 68
<211> LENGTH: 12
<212> TYPE: PRT
<213> ORGANISM: Artificial sequence
<220> FEATURE:
<223> OTHER INFORMATION: peptide

<400> SEQUENCE: 68

Leu Gln Thr Ala Pro Val Pro Met Pro Asp Leu Lys
1               5                   10

<210> SEQ ID NO 69
<211> LENGTH: 28
<212> TYPE: PRT
<213> ORGANISM: Artificial sequence
<220> FEATURE:
<223> OTHER INFORMATION: peptide

<400> SEQUENCE: 69

Gln Glu Phe Asp Thr Met Glu Asp His Ala Gly Asp Tyr Thr Leu Leu
1               5                   10                  15

Gln Asp Gln Glu Gly Asp Met Asp His Gly Leu Lys
            20                  25

<210> SEQ ID NO 70
<211> LENGTH: 19
```

```
<212> TYPE: PRT
<213> ORGANISM: Artificial sequence
<220> FEATURE:
<223> OTHER INFORMATION: peptide

<400> SEQUENCE: 70

Gln Glu Phe Glu Val Met Ile Glu Asp His Ala Gly Thr Tyr Gly Leu
1               5                   10                  15

Gly Asp Arg

<210> SEQ ID NO 71
<211> LENGTH: 18
<212> TYPE: PRT
<213> ORGANISM: Artificial sequence
<220> FEATURE:
<223> OTHER INFORMATION: peptide

<400> SEQUENCE: 71

Gln Glu Phe Glu Val Met Glu Asp His Ala Gly Thr Tyr Gly Leu Gly
1               5                   10                  15

Asp Arg

<210> SEQ ID NO 72
<211> LENGTH: 15
<212> TYPE: PRT
<213> ORGANISM: Artificial sequence
<220> FEATURE:
<223> OTHER INFORMATION: peptide

<400> SEQUENCE: 72

Ser Pro His Pro Val Val Ser Gly Asp Thr Ser Pro His Pro Arg
1               5                   10                  15

<210> SEQ ID NO 73
<211> LENGTH: 13
<212> TYPE: PRT
<213> ORGANISM: Artificial sequence
<220> FEATURE:
<223> OTHER INFORMATION: peptide

<400> SEQUENCE: 73

Ser Pro His Pro Val Val Ser Gly Asp Thr Ser Pro Arg
1               5                   10

<210> SEQ ID NO 74
<211> LENGTH: 24
<212> TYPE: PRT
<213> ORGANISM: Artificial sequence
<220> FEATURE:
<223> OTHER INFORMATION: peptide

<400> SEQUENCE: 74

Ser Pro His Thr Pro Thr Pro His Ala Glu Asp Val Thr Ala Pro Leu
1               5                   10                  15

Val Asp Glu Gly Ala Pro Gly Lys
            20

<210> SEQ ID NO 75
<211> LENGTH: 20
<212> TYPE: PRT
<213> ORGANISM: Artificial sequence
<220> FEATURE:
<223> OTHER INFORMATION: peptide

<400> SEQUENCE: 75
```

```
Ser Pro His Thr Pro Thr Pro His Ala Glu Asp Val Thr Ala Pro Leu
1               5                   10                  15

Val Asp Glu Arg
            20

<210> SEQ ID NO 76
<211> LENGTH: 22
<212> TYPE: PRT
<213> ORGANISM: Artificial sequence
<220> FEATURE:
<223> OTHER INFORMATION: peptide

<400> SEQUENCE: 76

Ser Pro His Thr Pro Thr Ala Glu Asp Val Thr Ala Pro Leu Val Asp
1               5                   10                  15

Glu Gly Ala Pro Gly Lys
            20

<210> SEQ ID NO 77
<211> LENGTH: 18
<212> TYPE: PRT
<213> ORGANISM: Artificial sequence
<220> FEATURE:
<223> OTHER INFORMATION: peptide

<400> SEQUENCE: 77

Ser Pro His Thr Pro Thr Ala Glu Asp Val Thr Ala Pro Leu Val Asp
1               5                   10                  15

Glu Arg

<210> SEQ ID NO 78
<211> LENGTH: 19
<212> TYPE: PRT
<213> ORGANISM: Artificial sequence
<220> FEATURE:
<223> OTHER INFORMATION: peptide

<400> SEQUENCE: 78

Ser Gly Tyr Ser Ser Pro Gly Ser Pro His Pro Gly Thr Pro His Pro
1               5                   10                  15

Gly Ser Arg

<210> SEQ ID NO 79
<211> LENGTH: 17
<212> TYPE: PRT
<213> ORGANISM: Artificial sequence
<220> FEATURE:
<223> OTHER INFORMATION: peptide

<400> SEQUENCE: 79

Ser Gly Tyr Ser Ser Pro Gly Ser Pro His Pro Gly Thr Pro Gly Ser
1               5                   10                  15

Arg

<210> SEQ ID NO 80
<211> LENGTH: 17
<212> TYPE: PRT
<213> ORGANISM: Artificial sequence
<220> FEATURE:
<223> OTHER INFORMATION: peptide

<400> SEQUENCE: 80

Ser Gly Tyr Ser Ser Pro Gly Ser Pro Gly Thr Pro His Pro Gly Ser
1               5                   10                  15
```

Arg

<210> SEQ ID NO 81
<211> LENGTH: 15
<212> TYPE: PRT
<213> ORGANISM: Artificial sequence
<220> FEATURE:
<223> OTHER INFORMATION: peptide

<400> SEQUENCE: 81

Ser Gly Tyr Ser Ser Pro Gly Ser Pro Gly Thr Pro Gly Ser Arg
1               5                   10                  15

<210> SEQ ID NO 82
<211> LENGTH: 13
<212> TYPE: PRT
<213> ORGANISM: Artificial sequence
<220> FEATURE:
<223> OTHER INFORMATION: peptide

<400> SEQUENCE: 82

Ser Pro Val Val Ser Gly Asp Thr Ser Pro His Pro Arg
1               5                   10

<210> SEQ ID NO 83
<211> LENGTH: 11
<212> TYPE: PRT
<213> ORGANISM: Artificial sequence
<220> FEATURE:
<223> OTHER INFORMATION: peptide

<400> SEQUENCE: 83

Ser Pro Val Val Ser Gly Asp Thr Ser Pro Arg
1               5                   10

<210> SEQ ID NO 84
<211> LENGTH: 22
<212> TYPE: PRT
<213> ORGANISM: Artificial sequence
<220> FEATURE:
<223> OTHER INFORMATION: peptide

<400> SEQUENCE: 84

Ser Thr Pro Thr Pro His Ala Glu Asp Val Thr Ala Pro Leu Val Asp
1               5                   10                  15

Glu Gly Ala Pro Gly Lys
            20

<210> SEQ ID NO 85
<211> LENGTH: 18
<212> TYPE: PRT
<213> ORGANISM: Artificial sequence
<220> FEATURE:
<223> OTHER INFORMATION: peptide

<400> SEQUENCE: 85

Ser Thr Pro Thr Pro His Ala Glu Asp Val Thr Ala Pro Leu Val Asp
1               5                   10                  15

Glu Arg

<210> SEQ ID NO 86
<211> LENGTH: 20
<212> TYPE: PRT
<213> ORGANISM: Artificial sequence
<220> FEATURE:

<223> OTHER INFORMATION: peptide

<400> SEQUENCE: 86

Ser Thr Pro Thr Ala Glu Asp Val Thr Ala Pro Leu Val Asp Glu Gly
1               5                   10                  15

Ala Pro Gly Lys
            20

<210> SEQ ID NO 87
<211> LENGTH: 16
<212> TYPE: PRT
<213> ORGANISM: Artificial sequence
<220> FEATURE:
<223> OTHER INFORMATION: peptide

<400> SEQUENCE: 87

Ser Thr Pro Thr Ala Glu Asp Val Thr Ala Pro Leu Val Asp Glu Arg
1               5                   10                  15

<210> SEQ ID NO 88
<211> LENGTH: 10
<212> TYPE: PRT
<213> ORGANISM: Artificial sequence
<220> FEATURE:
<223> OTHER INFORMATION: peptide

<400> SEQUENCE: 88

Val Asp Pro Ser Val Tyr Pro Leu Asp Arg
1               5                   10

<210> SEQ ID NO 89
<211> LENGTH: 13
<212> TYPE: PRT
<213> ORGANISM: Artificial sequence
<220> FEATURE:
<223> OTHER INFORMATION: peptide

<400> SEQUENCE: 89

Glu Gly Asp Pro Tyr Tyr Gly Tyr Thr Gly Ala Phe Arg
1               5                   10

<210> SEQ ID NO 90
<211> LENGTH: 10
<212> TYPE: PRT
<213> ORGANISM: Artificial sequence
<220> FEATURE:
<223> OTHER INFORMATION: peptide

<400> SEQUENCE: 90

Asp Ser Asp Pro Ala Tyr Gly Phe Phe Lys
1               5                   10

<210> SEQ ID NO 91
<211> LENGTH: 9
<212> TYPE: PRT
<213> ORGANISM: Artificial sequence
<220> FEATURE:
<223> OTHER INFORMATION: peptide

<400> SEQUENCE: 91

Val Glu Asp Pro Ser Trp Ile Leu Arg
1               5

<210> SEQ ID NO 92
<211> LENGTH: 10
<212> TYPE: PRT

```
<213> ORGANISM: Artificial sequence
<220> FEATURE:
<223> OTHER INFORMATION: peptide

<400> SEQUENCE: 92

Ser Ser Asp Pro Leu Val Ile Gln Trp Arg
1               5                   10

<210> SEQ ID NO 93
<211> LENGTH: 12
<212> TYPE: PRT
<213> ORGANISM: Artificial sequence
<220> FEATURE:
<223> OTHER INFORMATION: peptide

<400> SEQUENCE: 93

Cys Ile Pro Asp Phe Val Asn Ala Ala Phe Gly Lys
1               5                   10

<210> SEQ ID NO 94
<211> LENGTH: 38
<212> TYPE: PRT
<213> ORGANISM: Artificial sequence
<220> FEATURE:
<223> OTHER INFORMATION: peptide

<400> SEQUENCE: 94

Thr Cys Thr Thr Pro Ala Gln Gly Asn Ser Met Phe Pro Ser Cys Cys
1               5                   10                  15

Cys Thr Lys Pro Thr Asp Gly Asn Cys Thr Cys Ile Pro Ile Pro Ser
            20                  25                  30

Ser Trp Ala Phe Ala Lys
        35

<210> SEQ ID NO 95
<211> LENGTH: 22
<212> TYPE: PRT
<213> ORGANISM: Artificial sequence
<220> FEATURE:
<223> OTHER INFORMATION: peptide

<400> SEQUENCE: 95

Thr Cys Thr Thr Pro Ala Gln Gly Asn Ser Met Phe Pro Ser Cys Cys
1               5                   10                  15

Cys Thr Lys Pro Thr Asp
            20

<210> SEQ ID NO 96
<211> LENGTH: 16
<212> TYPE: PRT
<213> ORGANISM: Artificial sequence
<220> FEATURE:
<223> OTHER INFORMATION: peptide

<400> SEQUENCE: 96

Gly Asn Cys Thr Cys Ile Pro Ile Pro Ser Ser Trp Ala Phe Ala Lys
1               5                   10                  15

<210> SEQ ID NO 97
<211> LENGTH: 19
<212> TYPE: PRT
<213> ORGANISM: Artificial sequence
<220> FEATURE:
<223> OTHER INFORMATION: peptide

<400> SEQUENCE: 97
```

Lys Thr Cys Thr Thr Pro Ala Gln Gly Asn Ser Met Phe Pro Ser Cys
1               5                   10                  15

Cys Cys Thr

<210> SEQ ID NO 98
<211> LENGTH: 19
<212> TYPE: PRT
<213> ORGANISM: Artificial sequence
<220> FEATURE:
<223> OTHER INFORMATION: peptide

<400> SEQUENCE: 98

Lys Pro Thr Asp Gly Asn Cys Thr Cys Ile Pro Ile Pro Ser Ser Trp
1               5                   10                  15

Ala Phe Ala

<210> SEQ ID NO 99
<211> LENGTH: 19
<212> TYPE: PRT
<213> ORGANISM: Artificial sequence
<220> FEATURE:
<223> OTHER INFORMATION: peptide

<400> SEQUENCE: 99

Thr Cys Thr Thr Pro Ala Gln Gly Asn Ser Met Phe Pro Ser Cys Cys
1               5                   10                  15

Cys Thr Lys

<210> SEQ ID NO 100
<211> LENGTH: 19
<212> TYPE: PRT
<213> ORGANISM: Artificial sequence
<220> FEATURE:
<223> OTHER INFORMATION: peptide

<400> SEQUENCE: 100

Pro Thr Asp Gly Asn Cys Thr Cys Ile Pro Ile Pro Ser Ser Trp Ala
1               5                   10                  15

Phe Ala Lys

<210> SEQ ID NO 101
<211> LENGTH: 9
<212> TYPE: PRT
<213> ORGANISM: Artificial sequence
<220> FEATURE:
<223> OTHER INFORMATION: peptide

<400> SEQUENCE: 101

Leu Gly Pro Leu Val Glu Gln Gly Arg
1               5

<210> SEQ ID NO 102
<211> LENGTH: 18
<212> TYPE: PRT
<213> ORGANISM: Artificial sequence
<220> FEATURE:
<223> OTHER INFORMATION: peptide

<400> SEQUENCE: 102

Leu Gly Ala Thr Gln Ser Asn Glu Ile Thr Ile Pro Val Thr Phe Glu
1               5                   10                  15

Ser Arg

<210> SEQ ID NO 103
<211> LENGTH: 19
<212> TYPE: PRT
<213> ORGANISM: Artificial sequence
<220> FEATURE:
<223> OTHER INFORMATION: peptide

<400> SEQUENCE: 103

Asn Gly Val Pro Gln Glu Glu Ser Leu Glu Asp Ser Asp Val Asp Ala
1               5                   10                  15

Asp Phe Lys

<210> SEQ ID NO 104
<211> LENGTH: 14
<212> TYPE: PRT
<213> ORGANISM: Artificial sequence
<220> FEATURE:
<223> OTHER INFORMATION: peptide

<400> SEQUENCE: 104

Leu Gly Ala Ser Val Pro Gly Ser Gln Thr Val Val Val Lys
1               5                   10

<210> SEQ ID NO 105
<211> LENGTH: 9
<212> TYPE: PRT
<213> ORGANISM: Artificial sequence
<220> FEATURE:
<223> OTHER INFORMATION: peptide

<400> SEQUENCE: 105

Asn Gly Ile Ser Gln Val Leu Glu Lys
1               5

<210> SEQ ID NO 106
<211> LENGTH: 8
<212> TYPE: PRT
<213> ORGANISM: Artificial sequence
<220> FEATURE:
<223> OTHER INFORMATION: peptide

<400> SEQUENCE: 106

Asn Gly Phe Ser Ile Gln Val Arg
1               5

<210> SEQ ID NO 107
<211> LENGTH: 7
<212> TYPE: PRT
<213> ORGANISM: Artificial sequence
<220> FEATURE:
<223> OTHER INFORMATION: peptide

<400> SEQUENCE: 107

Asp Gly Val Thr Leu Gln Lys
1               5

<210> SEQ ID NO 108
<211> LENGTH: 13
<212> TYPE: PRT
<213> ORGANISM: Artificial sequence
<220> FEATURE:
<223> OTHER INFORMATION: peptide

<400> SEQUENCE: 108

Ser Gly Ile Pro Asp Asn Ala Phe Gln Ser Phe Gly Arg
1               5                   10

<210> SEQ ID NO 109
<211> LENGTH: 17
<212> TYPE: PRT
<213> ORGANISM: Artificial sequence
<220> FEATURE:
<223> OTHER INFORMATION: peptide

<400> SEQUENCE: 109

Leu Gly Leu Ile Phe Asp Thr Ser Asn Leu Gln Ser Gly Val Pro Ser
1               5                   10                  15

Arg

<210> SEQ ID NO 110
<211> LENGTH: 8
<212> TYPE: PRT
<213> ORGANISM: Artificial sequence
<220> FEATURE:
<223> OTHER INFORMATION: peptide

<400> SEQUENCE: 110

Leu Gly Pro Gln Thr Leu Ser Arg
1               5

<210> SEQ ID NO 111
<211> LENGTH: 14
<212> TYPE: PRT
<213> ORGANISM: Artificial sequence
<220> FEATURE:
<223> OTHER INFORMATION: peptide

<400> SEQUENCE: 111

Thr Pro His Pro Pro Gly Ser Pro His Gly Glu Pro Pro Lys
1               5                   10

<210> SEQ ID NO 112
<211> LENGTH: 12
<212> TYPE: PRT
<213> ORGANISM: Artificial sequence
<220> FEATURE:
<223> OTHER INFORMATION: peptide

<400> SEQUENCE: 112

Thr Pro His Pro Pro Gly Ser Gly Glu Pro Pro Lys
1               5                   10

<210> SEQ ID NO 113
<211> LENGTH: 9
<212> TYPE: PRT
<213> ORGANISM: Artificial sequence
<220> FEATURE:
<223> OTHER INFORMATION: peptide

<400> SEQUENCE: 113

Glu Gly Gln Leu Thr Pro Leu Ile Lys
1               5

<210> SEQ ID NO 114
<211> LENGTH: 12
<212> TYPE: PRT
<213> ORGANISM: Artificial sequence
<220> FEATURE:
<223> OTHER INFORMATION: peptide

<400> SEQUENCE: 114

Glu Gly Phe Asp Asp Leu Pro Leu Ala Glu Gln Arg

```
1               5                   10
```

<210> SEQ ID NO 115
<211> LENGTH: 15
<212> TYPE: PRT
<213> ORGANISM: Artificial sequence
<220> FEATURE:
<223> OTHER INFORMATION: peptide

<400> SEQUENCE: 115

```
Thr Gly Gln Ser Ser Leu Val Pro Ala Leu Thr Asp Phe Val Arg
1               5                   10                  15
```

<210> SEQ ID NO 116
<211> LENGTH: 9
<212> TYPE: PRT
<213> ORGANISM: Artificial sequence
<220> FEATURE:
<223> OTHER INFORMATION: peptide

<400> SEQUENCE: 116

```
Gly Ile Ala Pro Leu Gln Leu Gly Lys
1               5
```

<210> SEQ ID NO 117
<211> LENGTH: 14
<212> TYPE: PRT
<213> ORGANISM: Artificial sequence
<220> FEATURE:
<223> OTHER INFORMATION: peptide

<400> SEQUENCE: 117

```
Ile Ala Lys Pro Asn Val Ser Ala Ser Thr Gln Ala Ser Arg
1               5                   10
```

<210> SEQ ID NO 118
<211> LENGTH: 10
<212> TYPE: PRT
<213> ORGANISM: Artificial sequence
<220> FEATURE:
<223> OTHER INFORMATION: peptide

<400> SEQUENCE: 118

```
Thr Leu Asp Phe His Asp Ser Asn Val Lys
1               5                   10
```

<210> SEQ ID NO 119
<211> LENGTH: 8
<212> TYPE: PRT
<213> ORGANISM: Artificial sequence
<220> FEATURE:
<223> OTHER INFORMATION: peptide

<400> SEQUENCE: 119

```
Val Leu Pro Glu Asp Gly Pro Arg
1               5
```

<210> SEQ ID NO 120
<211> LENGTH: 8
<212> TYPE: PRT
<213> ORGANISM: Artificial sequence
<220> FEATURE:
<223> OTHER INFORMATION: peptide

<400> SEQUENCE: 120

```
Tyr Leu Gly Ala Asp Tyr Ile Lys
1               5
```

```
<210> SEQ ID NO 121
<211> LENGTH: 14
<212> TYPE: PRT
<213> ORGANISM: Artificial sequence
<220> FEATURE:
<223> OTHER INFORMATION: peptide

<400> SEQUENCE: 121

Thr Pro His Pro Pro Ser Ser Pro His Gly Glu Pro Pro Lys
1               5                   10

<210> SEQ ID NO 122
<211> LENGTH: 12
<212> TYPE: PRT
<213> ORGANISM: Artificial sequence
<220> FEATURE:
<223> OTHER INFORMATION: peptide

<400> SEQUENCE: 122

Thr Pro His Pro Pro Ser Ser Gly Glu Pro Pro Lys
1               5                   10

<210> SEQ ID NO 123
<211> LENGTH: 14
<212> TYPE: PRT
<213> ORGANISM: Artificial sequence
<220> FEATURE:
<223> OTHER INFORMATION: peptide

<400> SEQUENCE: 123

Thr Pro His Pro Ser Pro His Leu Pro Thr Pro Pro Thr Arg
1               5                   10

<210> SEQ ID NO 124
<211> LENGTH: 12
<212> TYPE: PRT
<213> ORGANISM: Artificial sequence
<220> FEATURE:
<223> OTHER INFORMATION: peptide

<400> SEQUENCE: 124

Thr Asp His Gly Ala Glu Ile Val Tyr Pro His Lys
1               5                   10

<210> SEQ ID NO 125
<211> LENGTH: 10
<212> TYPE: PRT
<213> ORGANISM: Artificial sequence
<220> FEATURE:
<223> OTHER INFORMATION: peptide

<400> SEQUENCE: 125

Thr Asp His Gly Ala Glu Ile Val Tyr Lys
1               5                   10

<210> SEQ ID NO 126
<211> LENGTH: 12
<212> TYPE: PRT
<213> ORGANISM: Artificial sequence
<220> FEATURE:
<223> OTHER INFORMATION: peptide

<400> SEQUENCE: 126

Thr Pro Pro Gly Ser Pro His Gly Glu Pro Pro Lys
1               5                   10
```

```
<210> SEQ ID NO 127
<211> LENGTH: 10
<212> TYPE: PRT
<213> ORGANISM: Artificial sequence
<220> FEATURE:
<223> OTHER INFORMATION: peptide

<400> SEQUENCE: 127

Thr Pro Pro Gly Ser Gly Glu Pro Pro Lys
1               5                   10

<210> SEQ ID NO 128
<211> LENGTH: 12
<212> TYPE: PRT
<213> ORGANISM: Artificial sequence
<220> FEATURE:
<223> OTHER INFORMATION: peptide

<400> SEQUENCE: 128

Thr Pro Pro Ser Ser Pro His Gly Glu Pro Pro Lys
1               5                   10

<210> SEQ ID NO 129
<211> LENGTH: 10
<212> TYPE: PRT
<213> ORGANISM: Artificial sequence
<220> FEATURE:
<223> OTHER INFORMATION: peptide

<400> SEQUENCE: 129

Thr Pro Pro Ser Ser Gly Glu Pro Pro Lys
1               5                   10

<210> SEQ ID NO 130
<211> LENGTH: 12
<212> TYPE: PRT
<213> ORGANISM: Artificial sequence
<220> FEATURE:
<223> OTHER INFORMATION: peptide

<400> SEQUENCE: 130

Thr Pro Ser Pro His Leu Pro Thr Pro Pro Thr Arg
1               5                   10

<210> SEQ ID NO 131
<211> LENGTH: 10
<212> TYPE: PRT
<213> ORGANISM: Artificial sequence
<220> FEATURE:
<223> OTHER INFORMATION: peptide

<400> SEQUENCE: 131

Thr Pro Ser Leu Pro Thr Pro Pro Thr Arg
1               5                   10

<210> SEQ ID NO 132
<211> LENGTH: 11
<212> TYPE: PRT
<213> ORGANISM: Artificial sequence
<220> FEATURE:
<223> OTHER INFORMATION: peptide

<400> SEQUENCE: 132

Val Ala Val Val Arg Thr Pro His Pro Pro Lys
1               5                   10
```

```
<210> SEQ ID NO 133
<211> LENGTH: 9
<212> TYPE: PRT
<213> ORGANISM: Artificial sequence
<220> FEATURE:
<223> OTHER INFORMATION: peptide

<400> SEQUENCE: 133

Val Ala Val Val Arg Thr Pro Pro Lys
1               5

<210> SEQ ID NO 134
<211> LENGTH: 12
<212> TYPE: PRT
<213> ORGANISM: Artificial sequence
<220> FEATURE:
<223> OTHER INFORMATION: peptide

<400> SEQUENCE: 134

Val Gln Ile Val Tyr Lys Pro Val Asp Leu Ser Lys
1               5                   10

<210> SEQ ID NO 135
<211> LENGTH: 34
<212> TYPE: PRT
<213> ORGANISM: Artificial sequence
<220> FEATURE:
<223> OTHER INFORMATION: peptide

<400> SEQUENCE: 135

His Leu Ser Asn Val Ser Ser Pro His Thr Gly Ser Ile Asp Met Val
1               5                   10                  15

Asp Ser Pro Gln Leu Ala Thr Leu Ala Asp Glu Val Ser Ala Ser Leu
            20                  25                  30

Ala Lys

<210> SEQ ID NO 136
<211> LENGTH: 21
<212> TYPE: PRT
<213> ORGANISM: Artificial sequence
<220> FEATURE:
<223> OTHER INFORMATION: peptide

<400> SEQUENCE: 136

His Val Pro Gly Gly Gly Ser Val Gln Ile Val Tyr Pro His Lys Pro
1               5                   10                  15

Val Asp Leu Ser Lys
            20

<210> SEQ ID NO 137
<211> LENGTH: 19
<212> TYPE: PRT
<213> ORGANISM: Artificial sequence
<220> FEATURE:
<223> OTHER INFORMATION: peptide

<400> SEQUENCE: 137

His Val Ser Gly Gly Gly Ser Val Gln Ile Val Tyr Lys Pro Val Asp
1               5                   10                  15

Leu Ser Lys

<210> SEQ ID NO 138
<211> LENGTH: 17
<212> TYPE: PRT
<213> ORGANISM: Artificial sequence
```

<220> FEATURE:
<223> OTHER INFORMATION: peptide

<400> SEQUENCE: 138

Ser Gly Tyr Ser Ser Pro His Pro Gly Ser Pro Gly Thr Pro Gly Ser
1               5                   10                  15

Arg

<210> SEQ ID NO 139
<211> LENGTH: 12
<212> TYPE: PRT
<213> ORGANISM: Artificial sequence
<220> FEATURE:
<223> OTHER INFORMATION: peptide

<400> SEQUENCE: 139

Thr Pro His Pro Ser Leu Pro Thr Pro Pro Thr Arg
1               5                   10

<210> SEQ ID NO 140
<211> LENGTH: 12
<212> TYPE: PRT
<213> ORGANISM: Artificial sequence
<220> FEATURE:
<223> OTHER INFORMATION: peptide

<400> SEQUENCE: 140

Thr Pro Ser Leu Pro Thr Pro His Pro Pro Thr Arg
1               5                   10

<210> SEQ ID NO 141
<211> LENGTH: 16
<212> TYPE: PRT
<213> ORGANISM: Artificial sequence
<220> FEATURE:
<223> OTHER INFORMATION: peptide

<400> SEQUENCE: 141

Gly Gly Phe Pro Glu Phe Val Asn Glu Leu His Asn Asn Gly Gln Lys
1               5                   10                  15

<210> SEQ ID NO 142
<211> LENGTH: 11
<212> TYPE: PRT
<213> ORGANISM: Artificial sequence
<220> FEATURE:
<223> OTHER INFORMATION: peptide

<400> SEQUENCE: 142

Glu Gly Ala Gln Leu Pro Val Ile Glu Asn Lys
1               5                   10

<210> SEQ ID NO 143
<211> LENGTH: 11
<212> TYPE: PRT
<213> ORGANISM: Artificial sequence
<220> FEATURE:
<223> OTHER INFORMATION: peptide

<400> SEQUENCE: 143

Ala Gly Ile Pro Asn Asn Gln Val Leu Gly Lys
1               5                   10

<210> SEQ ID NO 144
<211> LENGTH: 8
<212> TYPE: PRT

<213> ORGANISM: Artificial sequence
<220> FEATURE:
<223> OTHER INFORMATION: peptide

<400> SEQUENCE: 144

Ala Leu Val Gln Ile Val Gly Lys
1               5

<210> SEQ ID NO 145
<211> LENGTH: 9
<212> TYPE: PRT
<213> ORGANISM: Artificial sequence
<220> FEATURE:
<223> OTHER INFORMATION: peptide

<400> SEQUENCE: 145

Gly His Ser Gly Leu Gln Pro Gly Arg
1               5

<210> SEQ ID NO 146
<211> LENGTH: 15
<212> TYPE: PRT
<213> ORGANISM: Artificial sequence
<220> FEATURE:
<223> OTHER INFORMATION: peptide

<400> SEQUENCE: 146

Ala Ser Thr Pro Gly Ala Ala Ala Gln Ile Gln Glu Val Gly Lys
1               5                   10                  15

<210> SEQ ID NO 147
<211> LENGTH: 8
<212> TYPE: PRT
<213> ORGANISM: Artificial sequence
<220> FEATURE:
<223> OTHER INFORMATION: peptide

<400> SEQUENCE: 147

Val Val Asn Pro Thr Gln Gly Lys
1               5

<210> SEQ ID NO 148
<211> LENGTH: 11
<212> TYPE: PRT
<213> ORGANISM: Artificial sequence
<220> FEATURE:
<223> OTHER INFORMATION: peptide

<400> SEQUENCE: 148

Ile Pro Leu Glu Asn Leu Gln Ile Ile Gly Arg
1               5                   10

<210> SEQ ID NO 149
<211> LENGTH: 9
<212> TYPE: PRT
<213> ORGANISM: Artificial sequence
<220> FEATURE:
<223> OTHER INFORMATION: peptide

<400> SEQUENCE: 149

Asn Leu Ala Val Gln Ala Gln Gly Lys
1               5

<210> SEQ ID NO 150
<211> LENGTH: 10
<212> TYPE: PRT
<213> ORGANISM: Artificial sequence

```
<220> FEATURE:
<223> OTHER INFORMATION: peptide

<400> SEQUENCE: 150

Val Leu Asp Ala Leu Gln Ala Ile Gly Lys
1               5                   10

<210> SEQ ID NO 151
<211> LENGTH: 16
<212> TYPE: PRT
<213> ORGANISM: Artificial sequence
<220> FEATURE:
<223> OTHER INFORMATION: peptide

<400> SEQUENCE: 151

Val Thr Glu Pro Ile Ser Ala Glu Ser Gly Glu Gln Val Glu Gly Arg
1               5                   10                  15

<210> SEQ ID NO 152
<211> LENGTH: 15
<212> TYPE: PRT
<213> ORGANISM: Artificial sequence
<220> FEATURE:
<223> OTHER INFORMATION: peptide

<400> SEQUENCE: 152

Ile Ser Pro Asn Thr Ser Gln Gln Asn Phe Val Thr Gln Gly Arg
1               5                   10                  15

<210> SEQ ID NO 153
<211> LENGTH: 17
<212> TYPE: PRT
<213> ORGANISM: Artificial sequence
<220> FEATURE:
<223> OTHER INFORMATION: peptide

<400> SEQUENCE: 153

Phe Gln Ala Phe Ala Asn Gly Ser Leu Leu Ile Pro Asp Phe Gly Gly
1               5                   10                  15

Lys

<210> SEQ ID NO 154
<211> LENGTH: 13
<212> TYPE: PRT
<213> ORGANISM: Artificial sequence
<220> FEATURE:
<223> OTHER INFORMATION: peptide

<400> SEQUENCE: 154

Glu Pro Ile Ser Val Ser Ser Glu Gln Val Leu Gly Lys
1               5                   10

<210> SEQ ID NO 155
<211> LENGTH: 15
<212> TYPE: PRT
<213> ORGANISM: Artificial sequence
<220> FEATURE:
<223> OTHER INFORMATION: peptide

<400> SEQUENCE: 155

Ala Val Phe Gln Ala Asn Gln Glu Asn Leu Pro Ile Leu Gly Lys
1               5                   10                  15

<210> SEQ ID NO 156
<211> LENGTH: 12
<212> TYPE: PRT
```

```
<213> ORGANISM: Artificial sequence
<220> FEATURE:
<223> OTHER INFORMATION: peptide

<400> SEQUENCE: 156

Val Gln Pro Val Ser Glu Ile Leu Gln Leu Gly Lys
1               5                   10

<210> SEQ ID NO 157
<211> LENGTH: 10
<212> TYPE: PRT
<213> ORGANISM: Artificial sequence
<220> FEATURE:
<223> OTHER INFORMATION: peptide

<400> SEQUENCE: 157

Ala Leu Asp Val Ile Gln Ala Gly Gly Lys
1               5                   10

<210> SEQ ID NO 158
<211> LENGTH: 12
<212> TYPE: PRT
<213> ORGANISM: Artificial sequence
<220> FEATURE:
<223> OTHER INFORMATION: peptide

<400> SEQUENCE: 158

Ile Ile His Glu Ser Gly Ala Gln Ile Leu Gly Arg
1               5                   10

<210> SEQ ID NO 159
<211> LENGTH: 11
<212> TYPE: PRT
<213> ORGANISM: Artificial sequence
<220> FEATURE:
<223> OTHER INFORMATION: peptide

<400> SEQUENCE: 159

Glu Gln Leu Ser Ser Val Ser Ser Phe Glu Arg
1               5                   10

<210> SEQ ID NO 160
<211> LENGTH: 7
<212> TYPE: PRT
<213> ORGANISM: Artificial sequence
<220> FEATURE:
<223> OTHER INFORMATION: peptide

<400> SEQUENCE: 160

Gly Asp Val Ala Phe Val Lys
1               5
```